(12) United States Patent
Khatib

(10) Patent No.: US 7,807,361 B2
(45) Date of Patent: Oct. 5, 2010

(54) DAIRY CATTLE BREEDING FOR IMPROVED MILK PRODUCTION TRAITS IN CATTLE

(75) Inventor: Hasan Khatib, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 428 days.

(21) Appl. No.: 11/624,053

(22) Filed: Jan. 17, 2007

(65) Prior Publication Data

US 2008/0307535 A1 Dec. 11, 2008

Related U.S. Application Data

(63) Continuation-in-part of application No. 11/179,581, filed on Jul. 13, 2005.

(51) Int. Cl.
*C12Q 1/68* (2006.01)
*C07H 21/04* (2006.01)
*C12P 19/34* (2006.01)

(52) U.S. Cl. .......................... 435/6; 536/24.3; 435/91.2

(58) Field of Classification Search .................. None
See application file for complete search history.

(56) References Cited

FOREIGN PATENT DOCUMENTS

WO        WO 9511995 A1  *   5/1995

OTHER PUBLICATIONS

Mathialagan (Proceedings National Academy of Sciences (1996) vol. 13653-13658).*
GenBank accession L22095.1 GI:438480, (1997).*

* cited by examiner

*Primary Examiner*—Steven C Pohnert
(74) *Attorney, Agent, or Firm*—Kening Li; Pinsent Masons LLP

(57) ABSTRACT

Nucleic acid molecules comprising a SNP site at position 1296 of bovine uterine milk protein (UTMP) coding sequence (SEQ ID NO: 1), which SNP indicates a desirable productive life in a dairy cattle. Also disclosed are an array or a kit comprising the same, a method for detecting the SNPs, a method for progeny testing of cattle, and a method for selectively breeding of cattle.

8 Claims, 5 Drawing Sheets

Figure 1
Coding sequence for Bovine Uterine milk protein (UTMP)

```
   1    ggctggattg ccgcagaaat gtcccacggg agaatgaatc tggccctgtc tctggtcttc
  61    atcctctgtg gcctgtttaa tagcatcttc tgtgaaaagc aacaacactc tcaaaagcac
 121    atgaacctag tcttattaaa gaaaatttca gctctctccc agaagatgga agctcaccct
 181    aaggattttg cccaagaatt gttcaaggct ttgataattg aggatcccag aaagaatatc
 241    atcttctccc ccatggccat gaccaccacc ctggccaccc tctccctggg gatcaagtct
 301    acaatgagaa cccaccaccc tgaggacctg aaacttgagc ccaaactgtt ggatgtgcac
 361    aagtacttac agcctctggt ccacgtgggg cgtgagctag tgaagcagaa ggtactgaag
 421    caccagcaca ttctctttat caacagaaaa atgatggtca accagatgct tctacagcag
 481    ataagcaagc tgcagggaat ggacatccag atgattgact tacagatat agaaaaagcc
 541    aagaagacca tcagccacca tgtggctgaa aaaacacata cgaaaatcac aaacttaatc
 601    accgacctga accctgagac catcctgtgt cttgttaacc acattttctt caaaggcatc
 661    ttgaaaagag cttttcagcc caaactcacc cagaaggagg tcttctttgt gaatgaccaa
 721    accaaagtgc aggtggacat gatgagaaag acagaacgga tgctttacag ccggtcagag
 781    gagctacatg ctacgatggt taagatgcct tgcaaaggaa atgtgtccct aactctcatg
 841    cttccagatg ccggacaatt tgacactgat cttaaaaaga tgactgctaa gcgagctaaa
 901    cttcagaaaa tcagtgactt cagactggtg cgcttaattt tgcccaagtt gaagatctcc
 961    ttcaagataa actttaagca tctgcttccc aagattgacc ccaaacatat actgactgcc
1021    acagcaatct cacaggccat cacatcgaag gctcccctgc ctaatttgga ggccctacat
1081    caagctgaga tagagctgag cgagcacgcc ttaaccgtgg acacagccat tcacacagat
1141    aatctgttga aagtcccagt gaaggcaaag gaggtcccgg cggtcgtgaa agtcccaatg
1201    aaggcaaagg aggtcccggc ggtcgtgaaa gtcccaatga acacaaagga ggtcccagtg
1261    gtcgtgaaag tcccaatgaa cacaaaggag gtcccagtgg tcgtgaaggt caacagaccc
1321    ttcttgctgt tgtggagga tgaagagact caaagagacc tctttgtggg caaagtcctc
1381    aaccccccaag ttgagtagag ccagggccac actgtgcagc acaggaactt agcaggccat
1441    gaataaaaag agtacaattc acc
```

Notes: The SNP at position 1179 is A/G. G is the reported by the original submitter. The SNP at position 1296 is A/G. A is the nucleotide reported by the original submitter. The two SNPs are in the coding sequence, but do not change the amino acid sequence of the encoded polypeptide.

Figure 2
Coding sequence for bovine signal transducer and activator
of transcription (STAT1)

```
1    ctttaaatat agcctcaagt ttgccagtgg cttgcctgtg aaatagtgca aagctgtcct
61   gtatctgggc agaggataaa agttatgtgt gttattatat tttccacact ggccattgaa
121  aactaaagat tctctttctt gggagaatta gcttttggta tggctttatg atgctggcta
181  atatcaatag aaggaagtaa actttacaaa ttcatgagta gtatcttcca tttcagcttt
241  aataccaaag ttgaatatat tctgccttca tcatgaaatt gaagttagta aatgaaactg
301  tcttcacagt tctatcaagg gagccaaaact attaacagct ctcttaaggc aaatcctatt
361  atttttcaa aaagttgaaa ttaattgtag atgtaaacaa actcagaaat ttaatgcatg
421  tttcataagt gggttcactt gtctttattg tttagtaaaa attttaaaat tgagaagaaa
481  aactagtaat tgacaaatca ttaggtggag attatgagaa tccaataatt tgaaaactca
541  tcctgtgtaa ctgccttgag aattgggtaa ttttcactgg caaatgtgta tctctcacaa
601  atacattaca gatggttcca ctaaaa
```

Notes: SNP is at position 213 (C/T), with C being the
nucleotide reported by the original submitter. Primers are
designed to be positioned at positions 11-31 and positions
306-325.

Figure 3
Partial genomic sequence of the region encoding bovine
osteopontin (OPN/SPP1)

```
7561 taattaactc taaatattaa aattctcaca attaaagaac aaccactcca aaaaatagcc
7621 accaagcagg ccatttgggc tggttaaatg gatcttccct gcctgttggg cttccctgat
7681 agctcagttg gtaaagcatc tgcctgcaac ttggaagacc cgggttcagt ccctgggtcg
7741 ggaagactcc ctggagaagg aaatggcaac cccctctagt actcttgcct ggaaaatttc
7801 catggactga ggaccctggt aggctaagag tcagacagaa ctgagcaact tcacttcact
7861 ttcctgcctg tttgtaaaag tgagcttagg acaccaattg atctgtcagg ttgtcttccg
7921 gcttaatcct tccacaatga ggctagaaaa ataagacctg ctttggatgg aaacagctaa
7981 cttttgaata aaaagttac gttgtatgat gtgcactgat ttgtgtcttt tcttcttcag
8041 aattctgtgt cctctgagga aactgatgac aacaaacaaa atgtgagtct ttgctttgat
8101 tctgatgtct gttgtgcctt agactcagga aggcactctt tctcctaatg acattgccca
8161 ggttcaaatt ccggcaaaat tccactagca aaccttcag gaactacttt ttattgggac
8221 tattaatagg gataagttaa atttgctttc cttaagattc tatttgaaga tgctgagaat
8281 ctataagaga agttagataa atgacccagg atatttgcaa atcagaagtg tgatagacat
8341 taactgagct atagtttcta cacatggata agagagtcac cttttgatta tccaggctaa
8401 tagggaggtg atttagttt tgggggtgtg cattaataca tggattctct gatccctga
8461 gaattttcat ttcaaataga aaaggtagtc tcacaattat gtatctgtat ttattggatc
8521 attgaaattt ggtaaattag tgtttattat gaacaaggaa aaacagtgtc attgatacaa
8581 atattataac tcatacgttt ggcttgaaa tatctgtgaa aatcgttttt atgagaaacc
8641 aagaaaaatg ccttagaata ggattccatt tacccttgtg ttaaagggga aattggaata
8701 agctcatttt agcatttaaa agccattaag tgctttgttg tgaatacaaa gattctaaaa
8761 ctaaataaag atagtaaaat actaatgcac tgtaaagcct aagggacagt aaaaaccctg
8821 acacccattt ttctggccat cttgatttct agaccctccc aagtaagtcc aatgaaagcc
8881 ctgagcaaac agacgatcta gatgacgatg atgataacag ccaggacgtc aactctaatg
8941 actccgacga cgctgaaacc actgatgacc ctgaccattc cgacgagtct caccattctg
9001 atgaatctga tgaagttgat tttcccactg atattccaac aatcgcagtt ttcactccgt
9061 ttatccctac ggaaagcgca aatgatggcc gaggtgatag tgtggcttac ggactgaagt
```

Notes: SNP is at position 8514 (C/T), with C being the
nucleotide reported by the original submitter. Primers are
designed to be positioned at positions 8316-8338 and
positions 8588-8606/7. Positions are numbered according to
the GenBank.

Figure 4
Coding Sequence for bovine lectin-like oxidized LDL receptor (OLR1)

```
1     gcttcactct ctcattcttg gaatacattt gaaaatgact gttgatgacc ccaagggtat
61    gaaagatcaa cttgatcaga agccaaatgg caagacagca aaaggttttg tttcctcttg
121   gaggtggtac cctgctgctg tgactctagg ggtcctttgt ctgggattac tggtgactgt
181   tatattgttg atactgcaat tatcccaggt ctctgatctc ataaagaaac agcaagcaaa
241   tattactcac caggaagata tcctggaggg acagatttta gcccagcgcc gatcagaaaa
301   atctgcccag gagtcacaga aggaactcaa agaaatgata gaaacccttg cccacaagct
361   ggatgagaaa tccaagaaac taatggaact tcaccgccag aacctgaatc tccaagaagt
421   tctgaaagag gcagcaaact attcaggtcc ttgtccccaa gactggctct ggcatgaaga
481   aaactgttac caatttttcct ctggctcttt taattgggaa aaaagccagg agaactgctt
541   gtctttggat gcccacttgc tgaagattaa tagcacagat gaactggaat tcatccagca
601   aatgattgcc cattccagtt tccccttctg gatggggttg tcaatgagga acccaatta
661   ctcgtggctt tgggaagatg gtactccttt gacgccccac ttgtttagaa ttcagggagc
721   tgtttcccgt atgtatcctt cagggacctg tgcatatatt caaaggggaa ctgttttgc
781   tgaaaactgc atttaactg cattcagtat atgtcaaaag aaggcgaatc tattgagagc
841   acagtgaatt tgaaggatct ggaggaaaag aaggaaacct ttgaattctc ttctggaatt
901   taagctatac ttcatcactt agatgtaaac cattagagcc cagggaaatg cctgctactg
961   gttgagtgca gaactcctta gcagagactg gcccagctgc ctggcacctt gatagcaaaa
1021  gttgcaattc cctctgtata tttttcccta acttgttcca agtcctcccc tgcaggactt
1081  cagagaagtc aattttctg tttccattgt ttctaagaac tgttgccta actcaaggtc
1141  acagcattt tctcactttt gtcctatgct ttcttctagg cattgtagag ttttagattt
1201  tacatggaaa tctagaactt attttagatt aatttctaag tgatatatgg atgtatggaa
1261  gttttctgtt tgtttttgc ttgtgagtat tcaattgttt ttgcaacatt tgctgaaaag
1321  actattcttc cttcactaca ttgcctttgc actgttgtca acaattatcc atacatgcct
1381  ggctctattt ctggattttc tattccttc catttattta tttattattc ttggcttaca
1441  acatcaccat gatattttga attctatggt tcttaatat atcttggaat cacatggtag
1501  tagttattca ttgttgttct tttttagagt tgtttggtta atctatgctt ttgtatttct
1561  gtcttaaatt ggcttgtcca tttctaaaaa aacttgaaat tttgaattgc actgaatcca
1621  tacataaatt tagggaaaat tgaattctta aaaatactga tttgttcaac tcatgaaaaa
1681  ggtgtattgc tctatttagg tattccttat tttctttaag caatgctttt taatgttctt
1741  tgtgtagata ttgttagatt atcatcatgt attttcacatt atttatgcta ctgtagatag
1801  tattgttatc atttgttgtt cttattttca aagtcttctg ctagtatgta gaattataat
1861  aaagtttgat attaatatt
```

Notes: SNP is at position 1070(C/A), with C being the nucleotide reported by the original submitter. Primers are designed to be positioned at positions 8316-8338 and positions 821-1090.

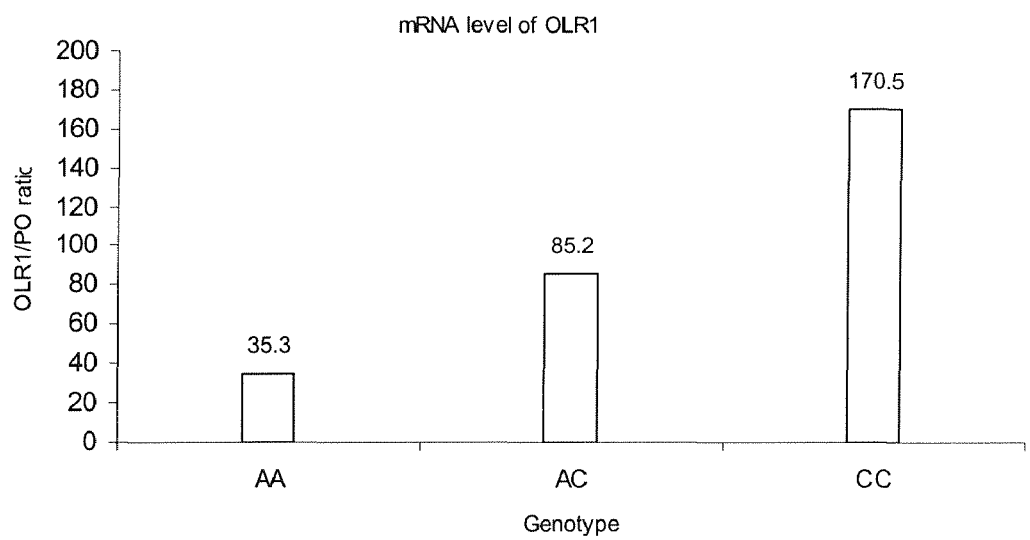
Fig. 5. Level of OLR1 mRNA in hearts from individuals with genotypes AA, AC, and CC at the 3' UTR SNP

DAIRY CATTLE BREEDING FOR IMPROVED MILK PRODUCTION TRAITS IN CATTLE

CROSS REFERENCE TO A RELATED APPLICATION

This application is a Continuation in Part of U.S. application Ser. No. 11/179,581 filed Jul. 13, 2005.

FEDERAL GOVERNMENT INTERESTS

This invention was made partially with United States government support awarded by USDA/CSREES, under the grant number 05-CRHF-0-6055. The United States may have certain rights in this application.

FIELD OF THE INVENTION

The present invention relates to a method of cattle progeny testing using molecular genetic methods by assaying for the presence of at least one genetic marker which is indicative of improved milk production traits, reproduction traits and animal heath traits, including milk yield and milk composition such milk fat content and milk protein content, somatic cell score, and productive life.

BACKGROUND OF THE INVENTION

Dairy cows are significant investments for dairy farmers, and enormous efforts, such as systematic animal breeding programs and artificial insemination, have been and continue to be invested in ensuring that the animals have high and sustained productivity, and that the milk produced is of high quality or has desired composition. A successful breeding family is the Holstein line derived from Carlin-M Ivenhoe Bell. More than 25% of the highest total performance index Holstein bulls in the United States are progenies of this individual.

Traditional breeding techniques involve the studying of sire progenies, and evaluating their milk production ratings (transmitting abilities) to guide further breeding. This standard technique requires years to evaluate the true genetic value by progeny testing each bull. Many cows must be bred and give birth to offspring. The females must be raised, bred, allowed to give birth and finally milked for a length of time to measure their phenotypic traits.

Furthermore, selection based purely on phenotypic characteristics does not efficiently take into account genetic variability caused by complex gene action and interactions, and the effect of environmental and developmental variants. There is thus a need for a method of genetically evaluating cattle to enable breeders to more accurately select animals at both the phenotypic and the genetic level.

Marker-assisted selection can lower the high cost and reduce the extended time commitment of progeny testing currently used to improve sires, since young bull progeny could be evaluated immediately after birth or even prior to birth for the presence/absence of the marker, and young bulls that are determined by genetic testing to have undesirable markers would never be progeny tested. Therefore, there is also a need for genetic markers for improved milk production traits.

SUMMARY OF THE INVENTION

It has been surprisingly discovered that dairy cattle whose genome has a certain genotype, specifically a single nucleotide polymorphism (SNP) exhibits highly desirable milk production traits. Specifically, (1) a cow whose bovine uterine milk protein (UTMP) coding sequence (FIG. 1; SEQ ID NO: 1) has a guanine at position 1296 (SNP 1) is found to have increased health/milk production life; (2) a cow whose signal transducer and activator of transcription (STAT1) coding sequence (FIG. 2; SEQ ID NO: 2) has a cytosine base at position 213 (SNP2) produces milk with increased milk fat yield, increased milk fat percentage, increased milk protein percentage. The thymine at position 213 is associated with a decrease in somatic cell score (SCS) versus the cytosine allele (3) a cow whose genomic sequence for the osteopontin (OPN) gene (see FIG. 3; SEQ ID NO: 3) has a cytosine base at position 8514 (SNP3) produces milk with increased milk protein percentage, and (4) a cow whose lectin-like oxidized LDL receptor (OLR1) coding sequence (FIG. 4; SEQ ID NO: 4) has an cytosine base at position 1070 (SNP4) produces milk with increased milk fat yield, increased milk fat percentage, and increased productive life.

The present invention provides an isolated nucleic acid molecule comprising a polymorphic site at position 1296 of FIG. 1 (SEQ ID NO: 1) and at least 15 contiguous nucleotides of the SEQ ID NO: 1 adjacent to the polymorphic site; an isolated nucleic acid molecule comprising a polymorphic site at position 213 of FIG. 2 (SEQ ID NO: 2) and at least 15 contiguous nucleotides of the SEQ ID NO: 2 adjacent to the polymorphic site; an isolated nucleic acid molecule comprising a polymorphic site at position 8514 of FIG. 3 (SEQ ID NO: 3) and at least 15 contiguous nucleotides of the SEQ ID NO: 3 adjacent to the polymorphic site; and an isolated nucleic acid molecule comprising a polymorphic site at position 1070 of FIG. 4 (SEQ ID NO: 4) and at least 15 contiguous bases of the SEQ ID NO: 1 adjacent to the polymorphic site.

Preferably, the nucleic acid molecule comprises i) a guanine base at position 1296 of SEQ ID NO: 1; ii) a cytosine base at position 213 of SEQ ID NO: 2; iii) a cytosine base at position 8514 of FIG. 3; or iv) a cytosine base at position 1070 of SEQ ID NO: 4.

Preferably, the nucleic acid molecule which comprises at least 17, more preferably at least 20, still more preferably at least 25, contiguous nucleotides (nt) of the respective sequences adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is near the 3'-end of the nucleic acid molecule. In another embodiment, the nucleic acid molecule contains the polymorphic site which is at the 3'-end of the nucleic acid molecule.

The present invention also provides an array of nucleic acid molecules comprising at least one of the nucleic acid molecules described above.

The present invention further provides a kit comprising the above-described nucleic acid molecule, and a suitable container. The kit preferably contains reagents useful for nucleotide amplification or detection.

Also provided is a method for detecting single nucleotide polymorphism (SNP) in a bovine polynucleotide comprising or coding for a sequence selected from the group consisting of SEQ ID NOs: 1, 2, 3 and 4, the method comprising determining the identity of a nucleotide at the respective polymorphic site of SEQ ID NOs: 1, 2, 3 or 4, and comparing the identity to the nucleotide at a corresponding position of the sequences respectively depicted in FIGS. 1, 2, 3 and 4.

In another embodiment, the present invention provides a method for genotyping a bovine cell, comprising determining the identity of at least one of the polymorphic sites described above. Suitable bovine cell may be an adult cell, an embryo cell, a sperm, an egg, a fertilized egg, or a zygote. The identity of the nucleotide may be determined by sequencing the aforementioned genes, or a relevant fragment thereof, isolated from the cell. The relevant gene or nucleic acid fragment may be isolated from a sample containing the cell via amplification by the polymerase chain reaction (PCR) of genomic DNA of the cell, or by RT-PCR of the mRNA of the cell. Preferably, the PCR or RT-PCR is conducted with a suitable pair of primers such as those depicted in FIG. 2, 3 or 4.

In a further embodiment, the present invention provides a method for progeny testing of cattle, the method comprising collecting a nucleic acid sample from the progeny, and genotyping the nucleic sample as described above.

Further provided is a method for selectively breeding of cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, and genotyping said developing embryo, and optionally terminating pregnancy if said developing embryo is not of a genotype having the desired SNP at one or more of the polymorphic positions described above.

In a preferred embodiment, the method is used for selectively breeding dairy cattle, comprising selecting a bull that has one or more of the desired genotype identified in the present invention and using its semen for fertilizing a female animal. More preferably, the female animal also has the desired genotype. Preferably, the male and female parents for the breeding program are homozygous with regard to the desired SNP allele. MOET procedure may be preferably used for the selective breeding.

The present invention also provides a method for testing dairy cattle for its milk production traits, comprising genotyping its cells, wherein cattle having a desired genotype indicates that the cattle has desirable milk production traits.

BRIEF DESCRIPTION OF THE DRAWINGS

FIG. 1 shows the coding sequence for bovine uterine milk protein (UTMP) (GenBank Accession No. L22095) (SEQ ID NO: 1.

FIG. 2 shows the coding sequence for bovine signal transducer and activator of transcription protein (STAT1) (GenBank Accession No. AW289395) (SEQ ID NO: 2), as well as the sequences and locations of the primers used in Example 2.

FIG. 3 shows the partial genomic sequence of the region encoding bovine osteopontin (OPN/SPP1) (GenBank Accession No. NW_255516) (SEQ ID NO: 3), as well as the sequences and locations of the primers used in Example 3.

FIG. 4 shows the coding sequence for bovine lectin-like oxidized LDL receptor (OLR1) (GenBank Accession No. D89049) (SEQ ID NO: 4), as well as the sequences and locations of the primers used in Example 4.

FIG. 5 shows a within-sire-family analysis for milk protein percentage in 14 heterozygous-sire families and 14 homozygous-sire families. The estimate of the effect of genotypes CC and CT on milk protein percentage was higher than the effect of the TT genotype in 17 families.

DETAILED DESCRIPTION OF THE INVENTION

The present inventor has identified four single nucleotide polymorphisms (SNPs) that are associated with improved milk production or animal health traits in dairy cattle. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker.

Details of the four SNPs of the present invention are described in Table 1.

TABLE 1

Summary of SNPs Associated with Improved Milk Production Traits

| Gene/Locus | Accession number | SNP and position | Trait associated | Significance of the gene (P) |
|---|---|---|---|---|
| Bovine Uterine milk protein (UTMP) | L22095 | (1296; A/G) | Productive Life | 0.0423 |
| Signal transducer and activator of | AW289395 | (213; C/T) C-allele | Milk fat percentage | 0.031 |

TABLE 1-continued

Summary of SNPs Associated with Improved Milk Production Traits

| Gene/Locus | Accession number | SNP and position | Trait associated | Significance of the gene (P) |
|---|---|---|---|---|
| transcription (STAT1) | | T-allele | Milk protein percentage<br>Somatic cell score | 0.0423<br>0.0527 |
| Osteopontin (OPN/SPP1) | NW_255516 | 8514 (C/T) | Milk protein percentage<br>Milk fat percentage | 0.0255<br>0.048 |
| OLR1 | D89049 | (1070; C/A) | Milk fat yield<br>Milk fat percentage | 0.00058<br>0.00001 |

The present invention also encompasses the complementary sequence corresponding to any of the provided polymorphisms. In order to provide an unambiguous identification of the specific site of a polymorphism, the numbering of the original sequences in the GenBank is shown and is used.

The present invention provides nucleic acid-based genetic markers for identifying bovine animals with superior reproduction and milk production traits. In general, for use as markers, nucleic acid fragments, preferably DNA fragments, will be of at least 10 to 12 nucleotides (nt), preferably at least 15 nt, usually at least 20 nt, often at least 50 nt. Such small DNA fragments are useful as primers for the polymerase chain reaction (PCR), and probes for hybridization screening, for use on a microarray etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridization a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at position 1296 of the bovine uterine milk protein (UTMP) coding sequence (FIG. 1; SEQ ID NO: 1) is guanine. An oligonucleotide probe can be used for such purpose. Preferably, the oligonucleotide probe will have a detectable label, and contain a cytosine (C) at the corresponding position. Experimental conditions can be chosen such that if the sample DNA contains an C, then the hybridization signal can be detected because the probe hybridizes to the corresponding complementary DNA strand in the sample, while if the sample DNA contains an A, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the genes. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other. Assays may utilize nucleic acids that hybridize to one or more of the described polymorphisms, and may include all or a subset of the polymorphisms listed in Table 1.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism at position 1296 of the UTMP gene may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the E. coli mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO 92/15712) and the ligase/polymerase mediated genetic bit analysis (U.S. Pat. No. 5,679,524). Related methods are disclosed in WO 91/02087, WO 90/09455, WO 95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide is described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the relevant genetic locus of the sample of interest may be amplified via PCR and directly sequenced, and the sequence be compared to the information of Table 1. In this case, two sets of PCR primers are preferably used for optimal amplification and to avoid the need to sequence an unnecessarily long fragment. Four such pairs of primers are depicted in FIGS. 1-4, respectively. It is readily recognized that numerous other primers can be devised to achieve the same objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected. The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers of the present invention.

The term "genotype" as used herein refers to the identity of the alleles present in an individual or a sample. In the context of the present invention, a genotype preferably refers to the description of the polymorphic alleles present in an individual or a sample. The term "genotyping" a sample or an individual for a polymorphic marker refers to determining the specific allele or the specific nucleotide carried by an individual at a polymorphic site.

The present invention is suitable for identifying a bovine, including a young or adult bovine animal, an embryo, a semen sample, an egg, a fertilized egg, or a zygote, or other cell or tissue sample therefrom, to determine whether said bovine possesses at least one of the SNPs of the present invention, which are indicative of improved milk production traits.

Further provided is a method for genotyping the bovine UTMP, STAT1, OPN, and OLR1 genes, comprising determining the nucleotide identity for the two copies of the genetic loci. One embodiment of a genotyping method of the invention involves examining both copies of the genes or coding sequences listed in Table 1, or a fragment thereof, to identify the nucleotide pair at one or more polymorphic sites listed in Table I in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele ("homozygous") or may be different alleles ("heterozygous"). In another embodiment, a genotyping method of the invention comprises determining the identity of the nucleotide pair at each of the polymorphic site listed in Table 1.

The present invention further provides a kit for detecting the SNPs of the present invention or for genotyping a bovine sample, the kit comprising in a container a nucleic acid molecule, as described above, designed for detecting the one or more of the polymorphisms listed in Table 1, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected for or removed from the breeding program. Preferably, individuals carrying at least one of SNPs 1, 2, 3 or 4 are selected. Preferably, these individuals are homozygous with regard to the SNP. For example, the individual is homozygous with regard to position 1296 (SNP1) of the UTMP gene and has a G at the position, or homozygous with regard to position 213 of the STAT 1 coding sequence and has a C at the position, or homozygous with regard to position 8514 of the OPN gene and has a C at the position, or homozygous with regard to position 1070 of the OLR1 coding sequence and has a C at the position.

The following examples are intended to illustrate preferred embodiments of the invention and should not be interpreted to limit the scope of the invention as defined in the claims.

EXAMPLES

Example 1

Pattern of Expression of the UMP gene and Its Association with Productive Life in Dairy Cattle The uterine milk proteins (UTMPs) are the major proteins secreted by the endometrium, primarily under the control of progesterone (Moffatt et al., 1987). Specific functions of UTMPs are poorly understood, but may include protease inhibition, nutrition of the conceptus, growth control, and suppression of the maternal immune system (1 ng and Roberts, 1989). Stewart et al. (2000) showed that ovine intracaruncular endometrial UTMP mRNA levels increased about 3 fold between days 20 and 60 of gestation, increased another 3 fold between days 60 and 80, and then declined slightly to day 120. Using Western blotting and immunohistochemistry, goat UTMP has been localized to the glandular epithelium of the endometrium at day 25 of pregnancy (Tekin et al., 2005). Leslie et al. (1990) found that UTMP was detected in the uterine fluid and secreted by the endometrium of pregnant cows. However, at present, it is not known whether the bovine UTMP gene is expressed in bovine tissues other than the endometrium. Our study aims at investigating the distribution of UTMP transcripts in a wide range of fetal and adult bovine tissues.

UTMP was chosen for this study because previous studies of the UTMP region have shown an association with productive life and milk composition traits in dairy cattle. Heyen et al. (1999) reported association between marker ILSTS054 and productive life in the North American Holstein population. Khatib et al. (2005) reported a significant association between the protease inhibitor gene (PI) and productive life and milk composition traits in Holstein dairy cattle. In addition, both PI and UTMP have protease inhibition functions, and the genes are both located on chromosome 21, within a 321.6 kb genomic region. Thus, possible roles of UTMP in health traits and its proximity to PI were the motives for investigation of possible effects of UTMP on health traits in dairy cattle.

Recent studies in humans (Yan et al., 2002; Bray et al., 2003; Lo et al., 2003; Pastinen et al., 2003), in mice (Cowles et al., 2002), and in maize (Guo et al., 2004) have shown that alleles of non-imprinted genes are not expressed equally at the mRNA level, and such differential allelic expression (DAE) may be the basis for variation in disease susceptibility and in determining phenotypic diversity. Yan et al. (2002) examined single nucleotide polymorphisms (SNPs) for 13 genes in 96 individuals and found significant differences in allelic variation in six out of the 13 genes studied, with 1.3-4.3 fold differences between alleles. In a survey of allelic variation among human genes, Pastinen et al. (2003) selected 129 genes based on their potential function in immune system and metabolic disorders and identified 18% of the genes with deviations from the equimolar ratio between the two alleles. Lo et al. (2003) examined allele-specific gene expression of 1063 transcribed SNPs by using the Affymetrix HuSNP chip system. The authors found that among the 602 genes that were heterozygous, 326 showed preferential expression of one allele in at least one individual, and 170 of those genes showed greater that fourfold difference between the two alleles.

It is noteworthy that there is accumulating evidence that DAE is associated with phenotypic variability of quantitative and qualitative traits. For example, Hirota and colleagues (2004) studied the relationship between DAE of the human cytochrome P450 3A4 (CYP3A4) gene and metabolic activity in the liver. Individuals displaying a large difference in expression levels between the two alleles showed reduced total CYP3A4 mRNA level and hence the total metabolic activity of the gene was reduced. This was the first study to demonstrate that CYP3A4 expression levels are affected by allele-specific expression levels.

The expression pattern of UTMP in fetal and adult cattle tissues was examined in this example, its association with production traits in two independent Holstein populations was investigated. In addition, the relationship between DAE of UTMP and association with quantitative traits was examined.

Materials and Methods

Tissue Collection and Nucleic Acid Extraction Tissues from 10 fetuses and 17 cattle dams were obtained from a local slaughterhouse. For nine of 10 fetuses, their dams were included in this study. Fetal tissues included lung, brain, bone, eye, heart, skeletal muscle, liver, cotyledon, spleen, pituitary, kidney, intestine, pancreas, mammary gland, testis, ovary, hypothalamus, and cartilage. The fetuses were at 55 to 100 days of age. The dams' tissues included endometrium, ovary, oocytes, liver, heart, spleen, kidney, caruncle, pancreas, lung, and skeletal muscle. After dissection, tissues were immediately chilled on ice and submerged in RNALater RNA stabilizing reagent (Qiagen, Valencia, Calif.). Total RNA was extracted using the RNeasy kit (Qiagen) and treated with DNase I (Sigma, St Louis, Mo.). DNA was extracted by grinding 30-100 mg of one tissue from each individual using the AquaPure Genomic DNA kit (Bio-Rad, Hercules, Calif.).

Reverse Transcriptase PCR(RT-PCR) Reverse transcription of the bovine UTMP gene was performed using the primers UMP1 (ATGTCCCACGGGAGAATGAA) (SEQ ID NO: 13) and UMP2 (CCTCCTTCTGGGTGAGTTTG) (SEQ ID NO: 14). The temperature cycles were as follows: 50° C. for 30 min (reverse transcription); 95° C. for 15 min, followed by 33 cycles of 94° C. for 1 min, 58° C. for 1 min, 72° C. for 1 min; and a final extension at 72° C. for 10 min. Primers b-actinF (CAGCACAATGAAGATCAAGAT-CATC) (SEQ ID NO: 15) and b-actinR (AAAGGGTG-TAACGCAGCTAACAGT) (SEQ ID NO: 16) were used to amplify 191 bp from the housekeeping gene b-actin (GenBank accession number NM_173979) cDNA. RT-PCR products were electrophoresed on a 1.5% agarose gel.

Phenotypic Data The association between UTMP variants and production traits was studied in two independent Holstein populations: the Cooperative Dairy DNA Repository (CDDR) and the University of Wisconsin daughter design resource population (henceforth: UW resource population). The UW population was created to search for genetic markers in association with susceptibility to paratuberculosis. The 12 sire families of this population were chosen from a large number of candidate bulls with large numbers of daughters in production in 2000. Criteria for the final selection of the 12 bulls included large numbers of daughters in production and relatively low pedigree relationships among the chosen bulls to more broadly sample the chromosomes of the US Holstein population. The CDDR phenotypic data referred to bulls' predicted transmitting abilities (PTA) data for milk yield (kg), milk protein and fat yields (kg), milk protein and fat percentages, productive life (month), and somatic cell score (points). The UW resource population data comprised cows' yield deviations for milk yield, milk protein and fat yields, and productive life (PL). Productive life is a longevity trait that is measured as a cow's total months in milking herd with limits of 10 months per lactation and seven years of age (VanRaden and Wiggans, 1995). Evaluations of PL are based on direct observations of length of productive life and also correlated traits measured earlier in life. The average reliabilities for PTA PL in the UW and CCDR populations are 39% and 71%, respectively. CDDR and UW phenotypic data were obtained from the Animal Improvement Programs Laboratory (Beltsville, Md.).

Polymorphism Detection and Genotyping Semen samples from 28 Holstein sires and their 1362 sons (23 to 104 sons per sire) were obtained from the CDDR population, which is maintained by the USDA Bovine Functional Genomics Laboratory. In addition, 913 blood samples were obtained from the UW resource population. For detailed description of this population see Cobanoglu et al. (2006). Genomic DNA was extracted from semen and blood samples using standard procedures. In order to detect single nucleotide polymorphisms (SNPs) in the UTMP gene (GenBank accession number L22095), DNA pools were constructed from 220 bovine samples and amplified with the primers UTMP3 (GGC-CCTACATCAAGCTGAGA) (SEQ ID NO: 17) and UTMP4 (CTACTCAACTTGGGGGTTGA) (SEQ ID NO: 18) as previously described (Leonard et al., 2005). PCR products of the pooled DNA samples were sequenced and SNPs were identified by visually inspecting sequence traces. For individual genotyping, primers UTMP3 and UTMP4 were used to amplify a 327-bp fragment of UTMP from genomic DNA. The PCR products were subjected to restriction fragment length polymorphism detection using the restriction enzyme BsrI that distinguishes alleles A and G of the SNP at position 1296. The digestion products were electrophoresed on a 3.0% agarose gel.

Allele Expression Quantification DAE of the UTMP gene was quantified by a sequencing-based approach and by single-nucleotide primer extension analysis. In the sequencing approach, RT-PCR products amplified from heterozygous individuals were sequenced according to standard procedures. Sequencing reactions of PCR amplicons were performed for 50 cycles at 96° C. for 10 sec, 58° C. for 4 min; and a final extension at 72° C. for 7 min. Data were analyzed using Applied Biosystems' Sequencing Analysis (version 5.0). SNPs were identified by visually inspecting each base in sequencing traces. Allelic variation was estimated by measuring the proportions of the peak heights of the two alternative alleles of the SNP. In the primer extension approach (Norton et al., 2002), RT-PCR products were purified from agarose gel using the GFX™ PCR DNA purification Kit (Amersham Biosciences). Primer extension reactions were prepared in a total volume of 10 µL containing 1 µL of purified RT-PCR product, 5 µL SnaPshot Kit (Applied Biosystems), 0.02 µM extension primer, and 1 µL deionized water. The primer extension reactions were subjected to 25 cycles of 96° C. for 10 sec, 50° C. for 5 sec, and 60° C. for 30 sec. In a post-extension treatment, reactions were treated with 1 unit of shrimp alkaline phosphatase at 37° C. for 1 hour followed by deactivation of the enzyme at 75° C. for 15 min. The primer 1179.ext (GTGAAGGCAAAGGAGGTCCC) (SEQ ID NO: 19) was used in the primer extension reactions. Samples were electrophoresed on a 3700 DNA sequencer (PE Applied Biosystems) and data were analyzed by using Genescan Analyzer version 2.5 software (PE Applied Biosystems). Allelic ratios were estimated by measuring the proportions of the peak heights of the two fluorescently labeled variants of the SNP found at the same position.

Statistical Analysis

For the CDDR population, data relative to each trait were analyzed using an allele substitution model expressed as:

$$y_{ij} = \mu + s_i + \beta x_{ij} + \epsilon_{ij},$$

where $y_{ij}$ is the PTA value relative to son j of sire i, $\mu$ is a general constant (intercept), $s_i$ is the fixed effect of sire i, $\beta$ is the regression coefficient representing half of the allele substitution effect ($\alpha/2$), $x_{ij}$ is the number of G alleles (0, 1, or 2) on son j of sire i, and $\epsilon_{ij}$ is a residual term. Reliabilities of the sons' PTAs were incorporated as weights in the model to obtain weighted least squares estimates of the allele substitution effects.

Data relative to the daughters in the UW resource population were analyzed using two models. First, an allele substitution model similar to the CDDR described above was considered, which is expressed as:

$$y_{ijk} = \mu + s_i + p_{ij}\tau + \beta x_k + \epsilon_{ijk},$$

where $y_{ijk}$ represents the yield deviation of daughter j of sire i, $\tau$ is an effect associated with *M. paratuberculosis* infection status, and $p_{ij}$ is an indicator variable assuming the values 0 and 1 for non-infected and infected cows, respectively. The index k indicates the genotype of the cows (k=AA, AG, or GG), and $x_k$ is the number of G alleles in the genotype k ($x_k$=0, 1, or 2, respectively). The remaining terms in the model are as previously defined. *M. paratuberculosis* infection status was included in the model because the UW population was originally created to search for genetic markers in association with susceptibility to paratuberculosis.

In addition, a second model was employed for each trait, which is described as:

$$y_{ijk} = \mu + s_i + p_{ij}\tau + g_k + \epsilon_{ijk},$$

where $g_k$ is the effect of the UTMP genotype k. Additive genetic effects were estimated as half of the difference between the two homozygous groups, and dominance effects were estimated as the difference between the average of the two homozygous groups and the heterozygous group. The AA genotype was set as baseline for estimating the genotypic effects. All the analyses were implemented using the GLM procedure of SAS (SAS Institute, 1999).

Results

Tissue Distribution of UTMP Expression in Fetuses and Dams Primers UMP1 and UMP2 were used to study the expression status of UTMP transcripts in a range of tissues obtained from 10 fetuses at ages between 55 and 100 days and 17 dams between 55 and 125 days of pregnancy. Expression of UTMP was assayed using RT-PCR amplification followed by agarose gel electrophoresis. Primers b-actinF and b-actinR were used to amplify the housekeeping gene b-actin as a control for the expression of UTMP in the various tissues. Table 2 shows the expression of the UTMP in a total of 93 fetal tissues. UTMP was expressed in all five cotyledon tissues examined. Two pituitary tissues expressed UTMP in which one tissue from fetus 2 (Day 65) showed low expression level. Ovary, hypothalamus, and spleen tissues showed low levels of expression in fetus 10 (Day 100). UTMP expression was not detected in eye, heart, skeletal muscle, lung, bone, kidney, pancreas, testis, mammary gland, adrenal, or intestine tissues in any of the fetuses examined. Table 3 shows the expression status of UTMP in 107 tissues obtained from 17 dams. Bovine UTMP was predominantly expressed in endometrium (17/17), ovary (15/16), and caruncle (12/12) tissues. Inconsistent amplification of UTMP was shown in liver, oocytes, spleen, and lung tissues. UTMP was expressed in the livers of 3 dams out of 6 examined, in which 2 liver tissues showed low expression levels. UTMP was expressed in one oocyte tissue out of 12 examined. Heart, skeletal muscle, kidney, and pancreas tissues did not express the UTMP gene in any examined individual.

TABLE 2

Expression pattern of UTMP transcripts obtained from various fetal tissues[1]

| Fetus (age in days) | Tissues expressing UTMP | Tissues not expressing UTMP |
|---|---|---|
| 1 (55) | | Eye, heart, , muscle, liver, lung, brain, bone |
| 2 (65) | Cotyledon, pituitary | Spleen, eye, lung, heart, kidney, intestine, pancreas, muscle, liver, bone, brain, mammary gland |
| 3 (68) | Cotyledon | Heart, muscle, eye, spleen, bone, lung, liver, kidney, testis, pituitary, pancreas, brain |
| 4 (68) | cotyledon | Mammary gland |
| 5 (70) | | Heart, muscle, brain, spleen, ovary |
| 6 (70) | | Liver, lung, brain, muscle, intestine, eye, bone, heart, kidney, ovary, pancreas, mammary gland |
| 7 (75) | | Lung, brain, eye, bone, testis, heart, kidney, muscle, pituitary, spleen, liver |
| 8 (85) | Cotyledon | Pituitary, spleen, lung, heart, brain, kidney, liver, muscle, adrenal, mammary gland, ovary |
| 9 (90) | cotyledon | Kidney |
| 10 (100) | Ovary, pituitary, hypothalamus, spleen | Lung, heart, pancreas, kidney, liver, bone, cartilage, mammary gland, muscle |

[1]Not all tissue types were examined in all fetuses

Association of UTMP with Productive Life in Two Independent Holstein Populations Using the pooled DNA sequencing approach, a SNP A/G at position 1179 and a SNP A/G at position 1296 were identified in the bovine UTMP gene. Genotyping of random samples revealed low polymorphism at SNP 1179; therefore it was not further analyzed in this study. For SNP 1296, frequency of allele G in the CDDR and UW populations was 0.72 and 0.64, respectively. The association between UTMP variants at position 1296 and production traits was tested in 1363 bulls from the CDDR and in 913 cows from the UW resource Holstein dairy cattle populations. SNP 1296 was associated with a significant increase in productive life in both populations. For the CDDR population, allele G was associated with a significant increase in productive life (P=0.008). Estimated allele substitution effects and their standard errors for production and health traits are given in Table 4. A bull inheriting allele G vs. allele A is expected to have, on average, 0.26 months higher PTA for productive life. For the UW resource population, allele G presented an average substitution effect of 1.44 months on productive life (P=0.033). UTMP variants did not show significant association with milk, fat, or protein yields or SCS in both populations studied (Table 4). Dominance and additive genetic effects were estimated for productive life and other traits using the UW resource population data. Dominance effects were not statistically significant for all traits. Additive genetic effect was significant only for productive life (P=0.049), with an estimate of 1.346±0.684 (SE) months.

TABLE 3

Expression pattern of UTMP transcripts obtained from various dams' tissues[1]

| Dam (estimated days into gestation) | Tissues expressing UTMP | Tissues not expressing UTMP |
|---|---|---|
| 1 (100) | Endometrium, ovary | Heart, kidney |
| 2 (100) | Endometrium, spleen, liver, | Heart, ovary, oocytes kidney, lung |
| 3 (85) | Endometrium, ovary, caruncle | Spleen, kidney |
| 4 (70) | Endometrium, ovary | Oocytes, pancreas, lung |
| 5 (55) | Endometrium, spleen | Liver, heart, muscle, oocytes, ovary, lung |
| 6 (75) | Endometrium, ovary, caruncle, liver | Heart, kidney, oocytes, spleen |

TABLE 3-continued

Expression pattern of UTMP transcripts obtained from various dams' tissues[1]

| Dam (estimated days into gestation) | Tissues expressing UTMP | Tissues not expressing UTMP |
|---|---|---|
| 7 (68) | Endometrium, ovary, caruncle, | Muscle, liver, lung, oocytes, heart, spleen |
| 8 (65) | Endometrium, ovary, caruncle, lung | Heart, muscle, liver, oocytes, pancreas |
| 9 (90) | Endometrium, ovary | Oocytes |
| 10 (68) | Endometrium, caruncle, ovary | Oocytes |
| 11 (90) | Endometrium, ovary, caruncle, oocytes, lung, spleen | Pancreas |
| 12 (85) | Endometrium, ovary, caruncle, spleen, liver | Heart, muscle, oocytes, pancreas, lung |
| 13 (83) | Endometrium, caruncle, lung | |
| 14 (90) | Endometrium, ovary, caruncle | Oocytes, lung, pancreas |
| 15 (75) | Endometrium, ovary, caruncle, | Oocytes, lung, pancreas |
| 16 (125) | Endometrium, caruncle, ovary, uterus | Heart, muscle, kidney |
| 17 (80) | Endometrium, caruncle, ovary | Heart, muscle |

[1]Not all tissues types were examined in all cows

Allelic Variation in UTMP Gene Expression In order to detect heterozygous individuals for allelic variation analysis, primers UMP3 and UMP4 were used to amplify genomic DNA from 10 fetuses and 17 dams. Fetus 10 and Dam 11 were heterozygous for the SNP (A/G) at position 1179, and five dams (Dams 2, 8, 12, 16, and 17) were heterozygous for the SNP (A/G) at position 1296. Then, primers UMP1 and UMP2 were used to amplify RT-PCR products from endometrium, ovary, and caruncle tissues obtained from the informative individuals. DAE was measured in tissues in which UTMP was highly expressed. Table 5 shows DAE of UTMP at SNP 1296 in these tissues, as measured by allelic ratios of G/A. UTMP displayed DAE in all heterozygous individuals examined. Allele G was preferentially expressed in all endometrium tissues. Extreme DAE was observed for two of three ovary tissues (monoallelic expression) and for two of four caruncle tissues (G/A allelic ratios of 2.50 and 4.00).

TABLE 4

Estimates of the allele substitution effect (of allele G) and standard errors for production and health traits in the CDDR and UW populations.

| | CDDR population | | UW resource population | |
|---|---|---|---|---|
| Trait | Estimate (SE) | P value | Estimate (SE) | P value |
| I. Fat yield | −0.188 (1.894) | 0.920 | −0.081 (4.30) | 0.985 |
| Fat percentage | 0.004 (0.008) | 0.573 | NR[1] | |
| Milk yield | −33.14 (51.52) | 0.520 | −120.7 (115.2) | 0.295 |
| Protein yield | −1.520 (1.290) | 0.237 | −2.093 (3.045) | 0.492 |
| Protein percentage | −0.002 (0.016) | 0.529 | NR[1] | |
| SCS | −0.016 (0.014) | 0.236 | 0.065 (0.067) | 0.336 |
| Productive life | 0.260 (0.098) | 0.008 | 1.443 (0.675) | 0.033 |

[1]NR-no records available for these traits.

TABLE 5

Allelic ratios of G/A alleles at SNP 1296 of UTMP in five heterozygous individuals for ovary, endometrium, and caruncle tissues.

| | Allelic ratios | | |
|---|---|---|---|
| Cow | Ovary | Endometrium | Caruncle |
| M2 | G[1] | 1.96 | ND[2] |
| M9 | ND[2] | 1.27 | 0.51 |
| M13 | G[1] | 1.78 | 4.00 |
| M20 | ND[2] | 1.81 | 1.56 |
| M21 | 0.50 | 1.81 | 2.30 |

[1]monoallelic expression of allele G;
[2]Not done

This is the first report on expression analysis of UTMP transcripts in a wide range of cattle tissues. UTMP expression was examined in a total of 198 tissues obtained from 10 fetuses and 17 dams. UTMP transcripts were found in all cotyledon tissues examined and to a less extent in ovary, pituitary, and spleen fetal tissues. UTMP transcripts were not found in any other fetal tissues examined.

To exclude the possibility of RT-PCR reaction failure in tissues where UTMP expression was not observed, beta-actin gene was amplified for all tissues. Expression of beta-actin gene was detected in all examined tissues, although there is a remote possibility of variable expression of beta-actin among the different tissues or individuals examined. Although the expression of UTMP in fetal tissues was surprising, its presence in reproductive tissues (cotyledon and ovary) might shed more light on the role of this gene in maintenance of pregnancy and fetal survival. Roberts and Bazer (1988) suggested that nutrition of the conceptus, growth control, and immunosuppression of the local maternal system are possible functions of the UTMPs.

The expression of UTMP has been mainly studied in sheep, with only a few studies on expression and localization of the bovine gene. In sheep, UTMP is the predominant protein present in the uterine fluid from day 30 of pregnancy until term (Moffatt et al., 1987). UTMP mRNA is not detected in endometrium until day 14 of pregnancy (Ing et al., 1989). In addition, mRNA levels of ovine UTMP have been found to be affected by day of pregnancy (Stewart et al., 2000). In this study, bovine UTMP was predominantly expressed in endometrium, ovary, and caruncle tissues in pregnant cows. Inconsistent amplification of RT-PCR products was observed in oocytes, lung, liver, and spleen tissues. On the other hand, heart, muscle, and pancreas tissues did not express UTMP in any examined individual. Thus the predominant expression of UTMP in reproductive tissues is consistent with an important role for this protein in reproductive success as previously suggested for the ovine gene (Ing and Roberts, 1989). However, in contrast to the aforementioned studies, this is the first report on expression of UTMP in tissues other than endometrium.

Two synonymous SNPs, at positions 1179 (A/G) and 1296 (A/G), were identified using the pooled DNA sequencing approach (Kwok et al., 1994; Khatib et al., 2006). SNP 1296 was associated with a significant increase in productive life. This finding parallels results previously obtained for the PI locus, which was also found to be associated with productive life in dairy cattle (Khatib et al., 2005; Heyen et al., 1999). Taken together, these results provide strong evidence that functionally the UTMP region is associated with productive life trait in dairy cattle.

There is accumulating evidence that allelic variation in gene expression is correlated with phenotypic variability of quantitative and qualitative traits. In humans, only a few studies have addressed the possible roles of allele-specific expression in phenotypic variability among individuals and in disease susceptibility (Murakami et al., 2004; Hirota et al., 2004; Duno et al., 2004). For example, Duno et al. (2004) examined DAE of the CLCN1 gene which causes myotonia congenita, an inherited disorder characterized by delayed skeletal muscle relaxation. Interestingly, they found that the expression level of the mutant allele was higher than that of the wild type allele, and they suggested that differential expression of CLCN1 alleles may have roles in progression of myotonia congenital disease.

In this study, a polymorphism-based approach was used to analyze the allelic variation in expression of the bovine UTMP gene in reproductive tissues obtained from 9 heterozygous individuals. RT-PCR analysis revealed that UTMP is expressed mainly in ovary, endometrium, and caruncle tissues. DAE of UTMP in these tissues was measured as an allelic ratio of G/A alleles at SNP 1296. All heterozygous individuals examined displayed DAE, with allele G preferentially expressed in all endometrium tissues. Monoallelic expression (allele G) was observed for two of three ovary tissues and for two of four caruncle tissues. It is generally believed that genes displaying DAE would cause phenotypic variability across individuals. Given that UTMP has possible roles in health traits and based on the constant preferential expression of G allele at SNP 1296, it is plausible that this SNP is functionally linked to improved productive life.

Thus, the DAE of the bovine UTMP gene observed in this study is consistent with other studies on different genes that have also shown a correspondence between allelic variation in gene expression and phenotypic variability.

In summary, this example showed that UTMP is primarily expressed in the bovine endometrium, ovary, and caruncle tissues, and there is significant association of SNP 1296 with increased productive life in two independent Holstein cattle populations. This SNP can be exploited by marker assisted selection for genetic improvement of productive life within a breeding nucleus or commercial population; or by marker assisted introgression for transferring desired alleles from a resource population to a commercial population.

References for Example 1

Bray, N. J., P. R. Buckland, M. J. Owen, and M. C. O'Donovan. 2003. Cis acting variation in the expression of a high proportion of genes in human brain. Hum. Genet. 113:149-153.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.

Cowles, C. R., J. N. Hirschhorn, D. Altshuler, and E. S. Lander. 2002. Detection of regulatory variation in mouse genes. Nat. Genet. 32:432-437.

Duno, M., E. Colding-Jorgensen, M. Grunnet, T. Jespersen, J. Vissing, and M. Schwartz. 2004. Difference in allelic expression of the CLCN1 gene and the possible influence on the myotonia congenita phenotype. Eur. J. Hum. Genet. 12:738-743.

Guo, M., M. A. Rupe, C. Zinselmeier, J. Habben, B. A. Bowen, and O, S. Smith. 2004. Allelic variation of gene expression in maize hybrids. Plant Cell 16:1707-1716.

Heyen, D. W., J. I. Weller, M. Ron, M. Band, J. E. Beever, E. Feldmesser, Y. Da, G. R. Wiggans, P. M. VanRaden, and H. A. Lewin. 1999. A genome scan for QTL influencing milk production and health traits in dairy cattle. Physiol. Genomics 1: 165-175.

Hirota, T., I. Jeiri, H. Takane, S. Maegawa, M. Hosokawa, K. Kobayashi, K. Chiba, E. Nanba, M. Oshimura, T. Sato, S. Higuchi, and K. Otsubo. 2004. Allelic expression imbalance of the human CYP3A4 gene and individual phenotypic status. Hum. Mol. Genet. 13:2959-2969.

Ing, N. H., and R. M. Roberts. 1989. The major progesterone-modulated proteins secreted into the sheep uterus are members of the serpin superfamily of serine protease inhibitors. J. Biol. Chem. 264:3372-3379.

Khatib, H., E. Heifetz, and J. C. Dekkers. 2005. Association of the protease inhibitor gene with production traits in Holstein dairy cattle. J. Dairy Sci. 88:1208-1213.

Khatib, H., S. Leonard, V. Schutzkus, W. Luo, and Y. M. Chang. 2006. Association of the OLR1Gene With Milk Composition in Holstein Dairy Cattle. J. Dairy Sci. 89:1753-1760.

Kwok, P. Y., C. Carlson, T. D. Yager, W. Ankener, and D. A. Nickerson. 1994. Comparative analysis of human DNA variations by fluorescence-based sequencing of PCR products. Genomics 23:138-144.

Leslie, M. V., P. J. Hansen, and G. R. Newton. 1990. Uterine secretions of the cow contain proteins that are immunochemically related to the major progesterone-induced proteins of the sheep uterus. Domest. Anim. Endocrinol. 7:517-526.

Lo, H. S., Z. Wang, Y. Hu, H. H. Yang, S. Gere, K. H. Buetow, and M. P. Lee. 2003. Allelic variation in gene expression is common in the human genome. Genome Res. 13:1855-1862.

Moffatt, J., F. W. Bazer, P. J. Hansen, P. W. Chun, and R. M. Roberts. 1987. Purification, secretion and immunocytochemical localization of the uterine milk proteins, major progesterone-induced proteins in uterine secretions of the sheep. Biol. Reprod. 36:419-430.

Murakami, Y., K. Isogai, H. Tomita, M. Sakurai-Yageta, T. Maruyama, A. Hidaka, K. Nose, K. Sugano, and A. Kaneko. 2004. Detection of allelic imbalance in the gene expression of hMSH2 or RB1 in lymphocytes from pedigrees of hereditary, nonpolyposis, colorectal cancer and retinoblastoma by an RNA difference plot. J. Hum. Genet. 49:635-641.

Norton, N., N. M. Williams, H. J. Williams, G. Spurlock, G. Kirov, D. W. Morris, B. Hoogendoom, M. J. Owen, and M. C. O'Donovan. 2002. Universal, robust, highly quantitative SNP allele frequency measurement in DNA pools. Hum. Genet. 110:471-478.

Pastinen, T., R. Sladek, S. Gurd, A. Sammak, B. Ge, P. Lepage, K. Layergne, A. Villeneuve, T. Gaudin, H. Brandstrom, A. Beck, A. Verner, J. Kingsley, E. Harmsen, D. Labuda, K. Morgan, M. C. Vohl, A. K. Naumova, D. Sinnett, and T. J. Hudson. 2003. A survey of genetic and epigenetic variation affecting human gene expression. Physiol. Genomics 16:184-193.

Roberts, R. M., and F. W. Bazer. 1988. The functions of uterine secretions. J. Reprod. Fertil. 82:875-892.

SAS Institute Inc. 1999. SAS User's Guide. SAS OnlineDoc, Version 8. SAS Institute Inc., Cary, N. C.

Stewart, M. D., G. A. Johnson, C. A. Gray, R. C. Burghardt, L. A. Schuler, M. M. Joyce, F. W. Bazer, and T. E. Spencer. 2000. Prolactin receptor and uterine milk protein expression in the ovine endometrium during the estrous cycle and pregnancy. Biol. Reprod. 62:1779-1789.

Tekin, S., M. B. Padua, G. R. Newton, and P. J. Hansen. 2005. Identification and cloning of caprine uterine serpin. Mol. Reprod. Dev. 70:262-270.

VanRaden, P. M., and G. R. Wiggans. 1995. Productive life evaluations: calculation, accuracy, and economic value. J. Dairy Sci. 78:631-638.

Yan, H., W. Yuan, V. E. Velculescu, B. Vogelstein, and K. W. Kinzler. 2002. Allelic variation in human gene expression. Science 297:1143.

Example 2

Effects of the Bovine STAT1 Variants on Production and Health Traits in Dairy Cattle Signal transducers and activators of transcription (STAT) factors are a family of cytoplasmic proteins that are activated by interaction with cytokines, growth factors, and hormones (Darnell 1997). The STAT proteins are activated via a cascade of phosphorylation events in which janus protein tyrosine kinases (JAKs) are first phosphorylated. STATs, in turn, become phosphorylated and they detach from the receptor complex. Then homo- or heterodimers of STATs translocate from the cytoplasm to the nucleus where they interact with promoter regions and regulate gene expression (Darnell 1997).

There is some evidence that STAT1 is involved in the development and differentiation of mammary gland. Boutinaud and Jammes (2004) measured the expression levels of STAT1, STAT3, and STAT5 in the mammary gland of lactating goats and found that the expression of these genes is regulated by growth hormone. Stewart et al. (1999) studied the regulation of STAT expression by effectors of adipocyte differentiation. They found that STAT1, STAT5A, and STAT5B are not exclusively regulated by individual effectors of differentiation, but their expression tightly correlates with lipid accumulation. Studies on the expression of STATs in different tissues and at different developmental stages have shown that STAT1 and STAT3 are constitutively expressed at constant levels through pregnancy, lactation, and involution while STAT4 and STAT5 are developmentally regulated (Watson 2001).

The bovine STAT1 maps to chromosome 2 at interval 60-63 cM (Band et al. 2000). Different whole genome scans have reported significant associations between production traits and microsatellite markers in the vicinity of STAT1. Mosig et al. (2001) reported a putative QTL affecting milk protein percentage in linkage with microsatellite marker BMS1126 at position 61.7 cM from the centromere. In addition, Ashwell et al. (2004) reported a QTL affecting milk fat percentage in linkage with microsatellites ETH121 and BM4440 at interval 38.0-60.3 cM. Also, Ron et al. (2004) reported a QTL affecting milk protein percentage at interval 61.7-70 cM from the centromere. These QTL studies, along with the studies on the function, involvement, and expression of STAT1 in mammary gland, prompted us to investigate the effects of this gene on production traits in dairy cattle.

By direct sequencing of genomic DNA, a single nucleotide polymorphism (SNP) in the EST corresponding to STAT1 (GenBank accession number AW289395) at position 213 was identified. Semen samples from 29 Holstein sires and their 1292 sons (average of 46 sons per sire) were obtained from the Cooperative Dairy DNA Repository, which is maintained by the USDA Bovine Functional Genomics Laboratory. Daughter yield deviations (DYD) data for milk yield, milk protein and fat yields, milk protein and fat percentages, and somatic cell score (SCS) were obtained from the Animal Improvement Programs Laboratory. The primers STATF: 5'-GCCTCAAGTTTGCCAGTGGC-3' (SEQ ID NO: 5) and STATR: 5'-GGCTCCCTTGATAGAACTGT-3' (SEQ ID NO: 6) were designed to amplify a fragment of 314 bp of genomic DNA. Amplification of genomic DNA was performed in 25 µl of reaction volume, which included 50 ng of genomic DNA, 50 ng of each primer, 200 µM of each dNTP, 2.5 µl of 10×PCR buffer (Promega, Madison, Wis.), and 0.3 units of Taq DNA polymerase (Promega). The temperature cycles were as follows: 95° C. for 5 min; 32 cycles of 94° C. for 45 s, touchdown annealing from 65° C.-53° C. for 45 s (−2° C./cycle), 72° C. for 45 s; and a final extension at 72° C. for 7 min.

The PCR products were digested with the restriction enzyme PagI that distinguishes alleles C and T of the SNP. The digestion products were electrophoresed on a 1.5% agarose gel; the T allele (uncut) was indicated by a band of 314 bp and the C allele was indicated by two bands of 201 and 113 bp. Weighted least squares analysis was employed to study the effects of STAT1 variants on production and functional traits. The model used was $$y_{ij} = \mu + sire_i + bx_{ij} + e_{ij}$$

where $y_{ij}$ is the DYD of the trait that was considered for son j of sire i, $sire_i$ is the fixed effect of sire i, b is the regression coefficient representing half of the gene substitution effect (Falconer and Mackey 1996), $x_{ij}$ is the number of C alleles (0, 1, or 2), and $e_{ij}$ is the residual. Reliability of the son's DYD was incorporated into the model to obtain weighted least squares estimates for the allele effects.

The analysis found a significant effect of STAT1 variants on milk fat percentage (P=0.0331), on milk protein percentage (P=0.0423), and on SCS (P=0.0527) in across family analysis (Table 6). The estimate of the increase in milk fat percentage of the C allele was 0.01%. The C allele was also associated with an increase in milk protein percentage versus the T allele (Table 6). Also, the T allele was associated with an increase in SCS versus the C allele.

TABLE 6

Estimated allele substitution effects (α/2) of the STAT1 C allele and standard error (SE) for milk production and health traits

| Trait | α/2(SE) | P |
| --- | --- | --- |
| Milk Fat yield | 1.76 (1.07) | 0.1011 |
| Milk fat percentage | 0.01 (0.004) | 0.0311 |
| Milk yield | 19.5 (29.7) | 0.5101 |
| Milk protein percentage | 0.004 (0.002) | 0.0423 |
| Milk protein yield | 0.51 (0.73) | 0.4888 |
| SCS | 0.019 (0.01) | 0.0527 |

The observed effects of the bovine STAT1 on milk composition and SCS traits was not surprising because of the following reasons:

1. The expression of STAT1 is under the control of the hormone prolactin. Following binding of prolactin to its receptor, a cascade of events is initiated that leads to activation of the STAT1, STAT3, and STAT5 proteins which in turn regulate the transcription of genes involved in secretion of milk proteins and components (Tucker 2000; Bole-Feysot et al. 2005).

2. Results in this example show that STAT1 was associated with milk fat and protein percentages. There is some evidence that STATs might be important for the regulation of fat metabolism and milk protein synthesis probably through the prolactin signal transduction pathway operating in the mammary gland (Mao et al. 2002).

3. Interferons regulate cellular antiviral, antiproliferative, and immunological responses. STAT1 has been shown to be essential for cell growth suppression in response to interferon-γ (Akira 1999). Moreover, it was reported that Stat1-deficient mice were found to be highly sensitive to infection by pathogens and they develop tumors more frequently than normal mice (Akira 1999; Watson 2001). These studies strongly indicate that STAT1 might have some roles in the immune response. The results in this example on the effect of STAT1 on somatic cells in milk, indicator for health in cows, are consistent with reported functions of this gene in the immune response of human and mouse.

Recently, the positional comparative candidate gene analysis and previous quantitative trait loci linkage mapping results were used to search for candidate genes affecting milk production traits, and a significant association between different haplotypes of the protease inhibitor gene and several production traits in Holstein dairy cattle including milk yield, milk fat yield, and SCS was found (Khatib et al. 2005). Using this approach STAT1 was chosen as a candidate gene affecting milk production traits References for Example 2

Akira S. (1999). Functional roles of STAT family proteins: lessons from knockout mice. Stem Cells 17, 138-46. 141

Ashwell M. S., Heyen D. W., Sonstegard T. S. et al. (2004). Detection of quantitative trait loci affecting milk production, health, and reproductive traits in Holstein cattle. Journal of Dairy Science 87, 468-75.

Band M. R., Larson J. H., Rebeiz M. et al. (2000). An ordered comparative map of the cattle and human genomes. Genome Research 10, 1359-68.

Bole-Feysot C., Goffin V., Edery M. et al. (2005). Prolactin (PRL) and its receptor: actions, signal transduction pathways and phenotypes observed in PRL receptor knockout mice. Endocrine Reviews 19, 225-68.

Boutinaud M. & Jammes H. (2004). Growth hormone increases Stat5 and Stat1 expression in lactating goat mammary gland: a specific effect compared to milking frequency. Domistic Snimal Endocrinology 27, 363-78.

Darnell J. E. (1997). STATs and gene regulation. Science 277, 1630-5. Falconer D. & Mackay T. F. (1996). Quantitative genetics. 4th ed. Addison Wesley Longman Ltd., Essex, England.

Khatib H., Heifetz E. & Dekkers J. C. (2005). Association of the protease inhibitor gene with production traits in Holstein dairy cattle. Journal of Dairy Science 88, 1208-13.

Mao J., Molenaar A. J., Wheeler T. T. & Seyfert H. M. (2002). STAT5 binding contributes to lactational stimulation of promoter III expressing the bovine acetyl-CoA carboxylase alpha-encoding gene in the mammary gland. Journal of Molecular Endocrinology 29, 73-88.

Mosig M. O., Lipkin E., Khutoreskaya G. et al. (2001). A whole genome scan for quantitative trait loci affecting milk protein percentage in Israeli-Holstein cattle, by means of selective milk DNA pooling in a daughter design, using an adjusted false discovery rate criterion. Genetics 157, 1683-98.

Ron M., Feldmesser E., Golik M. et al. (2004). A complete genome scan of the Israeli Holstein population for quantitative trait loci by a daughter design. Journal of Dairy Science 87, 476-90.

Stewart W. C., Morrison R. F., Young S. L. et al. (1999). Regulation of signal transducers and activators of transcription (STATs) by effectors of adipogenesis: coordinate regulation of STATs 1, 5A, and 5B with peroxisome proliferator-activated receptor-gamma and C/AAAT enhancer binding protein-alpha. Biochimica et Biophysica Acta 1452, 188-96.

Tucker H. A. (2000). Hormones, mammary growth, and lactation: a 41-year perspective. Journal of Dairy Science 83, 874-84.

Watson C. J. (2001). Stat transcription factors in mammary gland development and tumorigenesis. Journal of Mammary Gland Biology and Neoplasia 6, 115-27.

Example 3

Association of the Osteopontin Gene with Milk Protein Percentage in Dairy Cattle Osteopontin (OPN) is a highly phosphorylated glycoprotein whose gene has been cloned and sequenced in different species. Comparative sequence analysis of bovine OPN cDNA with various species has revealed both conserved and non-conserved sequences (Kerr et al. 1991). It was found, for example, that the bovine and ovine sequences have a 22 amino acid gap compared to all other examined species. Bovine OPN consists of six exons spanning about 7 kb of genomic DNA (Accession number NW_255516) and encodes a 278 amino acid protein (Kerr et al. 1991). Since its first description in 1979 as a protein associated with malignant transformation, OPN has been intensively studied in human, mouse, and sheep. It has been suggested that human OPN has various roles in cell adhesion, chemotaxis, cell survival, tissue remodeling, regulation of inflammation, fetal growth and development, and in initiating and maintaining pregnancy (Denhardt et al. 2001; Johnson et al. 2003).

Constitutive expression of OPN exists in several tissues, and the protein is present in milk, plasma, and urine. The OPN concentration in human milk ranges from 3 to 10 μg/ml (Senger et al. 1989). Using microarray analysis of RNA from human milk cells, Nagatomo et al. (2004) found that OPN showed the highest expression among 240 genes examined. They also found that both mRNA and protein levels were highly expressed throughout the entire lactation. The presence of OPN in milk and the high expression in mammary gland epithelial cells may account for the proliferation and differentiation of mammary glands (Nagatomo et al. 2004). The major sources of OPN were mammary gland epithelial cells and monocytes and macrophages in milk. OPN has also been detected in raw milk of cows at a concentration of 8 mg/L (Bayless et al. 1997). This has prompted us to investigate the effects of OPN on milk production traits in dairy cattle.

Previously, several whole genome scans have identified QTL affecting milk production traits on bovine chromosome 6 close to the OPN location (Zhang et al. 1998; Mosig et al. 2001; Ron et al. 2001; Nadesalingam et al. 2001; Rodriguez-Zas et al. 2002; Ashwell et al. 2004; Olsen et al. 2004). Ron and colleagues (2001) localized a QTL affecting protein percentage to a confidence interval of 4 cM in the region of OPN. Based on the aforementioned studies on the expression of OPN in the mammary gland and milk production QTL in the vicinity of the gene, possible associations between variants of the gene and milk production traits in Holstein dairy cattle were investigated.

Materials and Methods

Data Semen samples from 28 Holstein sires and their 1362 sons (19 to 102 sons per sire) were obtained from the Cooperative Dairy DNA Repository (CDDR), which is maintained by the USDA Bovine Functional Genomics Laboratory. In addition, 214 blood samples were obtained from the herd of the University of Wisconsin (UW herd). Predicted transmitting abilities (PTA) data for milk yield, milk protein and fat yields, milk protein and fat percentages, and SCS were obtained from the Animal Improvement Programs Laboratory. Summary statistics of PTA of both sons from the CDDR sire families and of cows from the UW herd for production and health traits is given in Table 7.

TABLE 7

Means, standard deviations (SD), and minimum, maximum, and average reliabilities (Rel) of predicted transmitting ability (PTA) of sons (from CDDR) and cows (UW herd) for production and health traits

| | CDDR | | | | | UW herd | | | | |
|---|---|---|---|---|---|---|---|---|---|---|
| Trait | Mean | SD | Min | Max | Rel | Mean | SD | Min | Max | Rel |
| Milk | 554 | 724 | −1743 | 2450 | 85.2 | 834 | 568 | −733 | 2375 | 55.6 |
| Fat | 18.40 | 22.41 | −59.00 | 81.00 | 85.2 | 28.34 | 20.34 | −27.00 | 87.00 | 55.6 |
| Protein | 21.84 | 20.21 | −55.00 | 85.00 | 85.1 | 27.11 | 15.05 | −19.00 | 67.00 | 55.6 |
| Fat % | −0.005 | 0.096 | −0.32 | 0.44 | 85.1 | −0.008 | 0.07 | −0.20 | 0.23 | 55.6 |
| Protein % | 0.023 | 0.044 | −0.14 | 0.18 | 85.1 | 0.01 | 0.03 | 0.09 | 0.11 | 55.6 |
| SCS | 3.14 | 0.16 | 2.68 | 3.71 | 70.5 | 3.12 | 0.13 | 2.74 | 3.53 | 40.6 |

Genotyping Genomic DNA was extracted from semen samples using proteinase K and phenol/chloroform after the procedures of Kappes et al. (2000) and from blood samples using GFX Genomic Blood DNA Purification Kit (Amersham Biosciences). The DNA concentration was measured using a spectrophotometer (Ultraspec 2100; Amersham Biosciences). A total of 1604 samples were genotyped in this study: 28 sires and their 1362 sons and 214 cows of the UW herd. In order to detect single nucleotide polymorphisms in OPN, different sets of primers were designed to amplify genomic sequences of the gene. Individuals were genotyped for a single nucleotide polymorphism (SNP) in intron 4 (GenBank accession number NW_255516) using the primers OPNF: GCAAATCAGAAGTGTGATAGAC (SEQ ID NO: 7) and OPNR: CCAAGCCAAACGTATGAGTT (SEQ ID NO: 8). Amplification of genomic DNA was performed in 25 μL of reaction volume, which included 50 ng of genomic DNA, 50 ng of each primer, 200 μM of each dNTP, 2.5 μL of 10×PCR buffer (Promega, Madison, Wis.), and 0.3 units of Taq DNA polymerase (Promega). The temperature cycles were as follows: 95° C. for 5 min; 32 cycles of 94° C. for 45 s, touchdown annealing from 63° C.-50° C. (−2° C./cycle) for 45s, 72° C. for 45 s; and a final extension at 72° C. for 7 min. The PCR products were subjected to restriction fragment length polymorphism (RFLP) using the restriction enzyme BsrI that distinguishes alleles C and T of the SNP. The digestion products were electrophoresed on a 1.5% agarose gel; the T allele (uncut) was indicated by a band of 290 bp and the C allele was indicated by a band of 200 bp.

Statistical analysis Maternal allele frequencies of OPN were estimated following Thaller et al. (2003), where all sons from homozygous sires and all homozygous sons of heterozygous sires were used. The allele frequencies were estimated using the formula:

$$P_c = \frac{n_{CC} + n'_{TC}}{n_{CC} + n'_{TC} + n'_{TT} + n_{TT}}$$

where $n_{CC}$ and $n_{TT}$ are the number of homozygous CC and TT sons within heterozygous sires; $n'_{TC}$ and $n'_{TT}$ are the number of heterozygous TC and homozygous TT sons from homozygous TT sires. Weighted least squares analysis was employed to study the effects of OPN variants on production and functional traits in both the CDDR and UW herd populations. The model was $$y_{ij} = \mu + Sire_i + \beta x_{ij} + e_{ij},$$

where $y_{ij}$ is the PTA of the trait that was considered for son (CDDR)/daughter (UW herd) j of sire i, $Sire_i$ is the fixed effect of sire i, β is the regression coefficient of PTA on the number of C alleles (0, 1, or 2) for jth son/daughter of sire i, and $e_{ij}$ is the residual. Reliability of the son's PTA was incorporated as weights in the model to obtain weighted least squares estimates for the allele substitution effects.

TABLE 8

Distribution of genotypes of sons for CDDR population.

| | Son genotypes | | |
|---|---|---|---|
| Sire genotype | CC | CT | TT |
| CC | 136 | 181 | 0 |
| CT | 181 | 392 | 196 |
| TT | 0 | 156 | 120 |

Results and Discussion

In this study, the frequencies of the OPN gene variants and their effects on milk production and health traits were examined in two independent Holstein populations. Table 8 shows the distribution of genotypes of sons and cows for the CDDR and UW herd populations, respectively. For the CDDR population, the number of sons per grandsire family ranged from 19 to 102 with an average of 49 sons per family. Seven sires were homozygous CC; seven sires were homozygous TT; and 14 sires were heterozygous. The estimated C allele frequency was 0.516 (±0.019). For the UW herd population, the frequencies of C and T alleles were 0.49 and 0.51, respectively. Thus, the frequencies of OPN alleles seem to be evenly distributed in both populations.

Table 9 shows the estimates of the allele substitution effects and their standard errors for production and health traits in the CDDR and UW herd populations. For the CDDR population, the C allele was associated with an increase in milk protein percentage (P=0.0255) and milk fat percentage (P=0.0480). The correlation between the two traits was 0.57 in the CDDR population (Khatib et al. 2005). OPN variants did not show significant effects on milk, fat, or protein yields or SCS. Although not statistically significant, allele C showed a negative effect on milk yield. This effect was not unexpected because of the negative correlation (−0.40) between this trait and milk protein percentage.

TABLE 9

Estimates of allele substitution effects and standard errors (SE) for production and health traits in the CDDR and UW herds

| Trait | CDDR population | | UW herd | |
|---|---|---|---|---|
| | α/2 (SE) | P | α/2 (SE) | P |
| Milk yield | −28 (24) | 0.2491 | −61 (64) | 0.3474 |
| Milk fat yield | 0.86 (0.88) | 0.3229 | −0.78 (2.50) | 0.7554 |
| Milk fat % | 0.008 (0.004) | 0.048 | 0.005 (0.009) | 0.5623 |
| Milk protein yield | 0.12 (0.60) | 0.8481 | −0.38 (1.70) | 0.8264 |
| Milk protein % | 0.004 (0.002) | 0.0255 | 0.006 (0.005) | 0.2568 |
| SCS | −0.002 (0.006) | 0.7165 | −0.020 (0.017) | 0.2348 |

For the UW herd population, the estimates of the effects of allele C were in the same direction (negative for milk yield and positive for milk protein percentage) as for the CDDR population, although these estimates did not reach statistical significance level. This could be due to the small number of animals (214) that were available for genotyping and phenotyping and low reliabilities of PTA for the cows (Table 7). However, the results of the UW herd did not contradict the findings in the CDDR population. It is worth noting that the C allele did not show any significant unfavorable effects on the other examined traits.

The results above are consistent with other studies that have shown a significant association of microsatellite markers in the region of OPN with milk protein percentage and other correlated traits (Zhang et al. 1998; Mosig et al. 2001; Ron et al. 2001; Nadesalingam et al. 2001; Rodriguez-Zas et al. 2002; Ashwell et al. 2004; Olsen et al. 2004). Recently, Olsen and colleagues (2005) positioned a QTL affecting milk production traits to an interval of 420 kb between the genes ABCG2 (ATP-binding cassette, sub-family G (WHITE), member 2) and LAP3 (leucine aminopeptidase 3) on bovine chromosome 6. This narrow region harbours only six genes including OPN. While reporting this study, Schnabel et al. (2005) reported that OPN was associated with milk protein percentage in the CDDR population. They searched for SNPs in about 5 kb of sequence upstream of bovine OPN and identified 6 SNPs in which one SNP (a deletion/insertion) showed significant association with milk protein percentage.

Although the causative mutation was not found in the above study nor in other studies (Schnabel et al. 2005), it is concluded that OPN affects milk protein percentage or it is in linkage disequilibrium with other gene(s) that do. Further investigation of the OPN gene including upstream and downstream control regions is needed to elucidate molecular mechanisms causing the QTL effects.

References for Example 3

Ashwell, M. S., D. W. Heyen, T. S. Sonstegard, C. P. Van Tassell, Y. Da, P. M. VanRaden, M. Ron, J. I. Weller, and H. A. Lewin. 2004. Detection of quantitative trait loci affecting milk production, health, and reproductive traits in Holstein cattle. J. Dairy Sci. 87:468-475.

Bayless K. J., G. E. Davis, and G. A. Meininger. 1997. Isolation and biological properties of osteopontin from bovine milk. Protein Expr Purif. 9:309-314.

Denhardt, D. T., M. Noda, A. W. O'Regan, D. Pavlin, and J. S. Berman. 2001. Osteopontin as a means to cope with environmental insults: regulation of inflammation, tissue remodeling, and cell survival. J Clin Invest. 107:1055-1061.

Johnson G. A., R. C. Burghardt, F. W. Bazer, and T. E. Spencer. 2003. Osteopontin: roles in implantation and placentation. Biol Reprod. 69:1458-1471.

Kerr J. M., L. W. Fisher, J. D. Termine, and M. F. Young. 1991. The cDNA cloning and RNA distribution of bovine osteopontin. Gene 108:237-243.

Khatib H., E. Heifetz, and J. C. Dekkers. 2005. Association of the protease inhibitor gene with production traits in Holstein dairy cattle. J. Dairy Sci. 88:1208-1213.

Mosig M. O., E. Lipkin, G. Khutoreskaya, E. Tchourzyna, M. Soller, and A. Friedmann. 2001. A whole genome scan for quantitative trait loci affecting milk protein percentage in Israeli-Holstein cattle, by means of selective milk DNA pooling in a daughter design, using an adjusted false discovery rate criterion. Genetics 157:1683-1698.

Nadesalingam, J., Y. Plante, J. P. Gibson. 2001. Detection of QTL for milk production on Chromosomes 1 and 6 of Holstein cattle. Mammalian Genome 12:27-31.

Nagatomo, T., S. Ohga, H. Takada, A. Nomura, S. Hikino, M. Imura, K. Ohshima, and T. Hara. 2004. Microarray analysis of human milk cells: persistent high expression of osteopontin during the lactation period. Clin Exp Immunol. 138:47-53.

Olsen, H. G., S. Lien, M. Svendsen, H. Nilsen, A. Roseth, M. Aasland Opsal, and T. H. E. Meuwissen. 2004. Fine Mapping of Milk Production QTL on BTA6 by Combined Linkage and Linkage Disequilibrium Analysis. J. Dairy Sci. 87:690-698.

Olsen, H. G., S. Lien, M. Gautier, H. Nilsen, A. Roseth, P. R. Berg, K. K Sundsaasen, M. Svendsen, and T. H. Meuwissen. 2005. Mapping of a milk production quantitative trait locus to a 420-kb region on bovine chromosome 6. Genetics 169:275-283.

Rodriguez-Zas, S. L., B. R. Southey, D. W. Heyen, and H. A. Lewin. 2002. Detection of Quantitative Trait Loci Influencing Dairy Traits Using a Model for Longitudinal Data. J. Dairy Sci. 85:2681-2691.

Ron, M., D. Kliger, E. Feldmesser, E. Seroussi, E. Ezra, and J. I. Weller. 2001. Multiple quantitative trait locus analysis of bovine chromosome 6 in the Israeli Holstein population by a daughter design. Genetics 159:727-735.

Schnabel, R. D., J. J. Kim, M. S. A-shwell, T. S. Sonstegard, C. P. Van Tassell, E. E. Connor, and J. F. Taylor. 2005. Fine-mapping milk production quantitative trait loci on BTA6: Analysis of the bovine osteopontin gene. Proc Natl Acad Sci USA. 102:6896-6901.

Senger D. R., C. A. Perruzzi, A. Papadopoulos, and D. G. Tenen. 1989. Purification of a human milk protein closely similar to tumor-secreted phosphoproteins and osteopontin. Biochim Biophys Acta. 996:43-48.

Thaller, G., W. Kramer, A. Winter, B. Kaupe, G. Erhardt, and R. Fries. 2003. Effects of DGAT1 variants on milk production traits in German cattle breeds. J. Anim Sci. 81:1911-1918.

Zhang, Q., D. Biochard, I. Hoeschele, C. Ernst, A. Eggen, B. Murkve, M. Pfister-Genskow, L. A. Witte, F. E. Grignola, P. Uimari, G. Thaller, and M. D. Bishop. 1998. Mapping QTL for milk production and health of dairy cattle in a large outbred pedigree. Genetics 149:1959-1973.

Example 4

Milk Composition is Affected by a Quantitative Trait Nucleotide in the 3' Untranslated Region of the OLR1 Gene The oxidized form of the low density lipoprotein (oxLDL) is involved in endothelial cell injury, dysfunction, and activation, which is implicated in the development of atherosclerosis (1). It has been shown that oxLDL, and its lipid constituents, have numerous damaging effects on secretory activities of the endothelium, including the induction of apoptosis (2). The major protein, oxidized LDL receptor (OLR1), that binds, internalizes, and degrades oxLDL was initially identified in bovine aortic endothelial cells by Sawamura et al. (3). In addition to binding oxLDL, OLR1 removes aged/apoptotic cells from blood circulation (4). The bovine OLR1 cDNA encodes 270 amino acids with a 72% sequence identity to the human protein (3). Aoyama et al. (5) determined the structure of the human OLR1 gene to include six exons in which the first three exons corresponded to the N-terminal cytoplasmic, transmembrane, and connecting neck domains, and the last three exons encoded the lectin domain. The genomic sequence of the bovine OLR1 gene, recently released by the Baylor College of Medicine, contains five exons (GenBank accession no. NW_215807).

The exact location of the bovine OLR1 is not known, but based on combined data from different cattle genetic maps available in public databases, the present inventor mapped the gene at the interval of 106-108 cM of chromosome 5. Several quantitative trait loci (QTL) affecting milk production traits have been reported on bovine chromosome 5 in the vicinity of OLR1 gene (6). Heyen et al. (7) reported a putative QTL affecting fat percentage at a position 100 cM from the centromere in a large granddaughter and daughter design population composed of 1068 sons and 3264 daughters, respectively. Olsen et al. (8) reported that a QTL affecting fat yield at position 115 cM from the centromere. Also, Ashwell et al. (9) reported that a QTL located at 87 cM was associated with fat percentage in a North American Holstein population. QTL for other milk production traits in the OLR1 region were also reported. De Koning et al. (10) reported that a QTL at position 107 cM was associated with milk yield in the Finnish Ayrshire population. Using the same population, Viitala et al. (11) reported another QTL at position 98 cM that was associated with milk yield. QTL for milk yield was also reported at position 109 cM by Bennewitz et al. (12). For protein yield, Rodriguez-Zas et al. (13) reported that a QTL affecting this trait was located at position 91 cM.

Based on the abovementioned studies on the role of human OLR1 in lipid metabolism including degradation of oxLD and on previous QTL studies, the present inventor chose OLR1 as a candidate gene for association tests with milk production traits in dairy cattle. Several lines of evidence are presented here for a quantitative trait nucleotide (QTN) in the 3' untranslated region (UTR) that significantly increases fat yield and fat percentage in milk.

This gene appears to be the first marker gene identified in dairy cattle that affects fat content without negatively affecting other useful traits.

Materials and Methods

Population and phenotypic data. Semen samples from 29 Holstein sires and their 1433 sons were obtained from the Cooperative Dairy DNA Repository (CDDR), which is maintained by the USDA Bovine Functional Genomics Laboratory. Predicted transmitting abilities (PTA) for milk yield, milk protein and fat yields, milk protein and fat percentages, productive life, and somatic cell score (SCS) were obtained from the USDA Animal Improvement Programs Laboratory. DNA samples from 19 Brown Swiss, 18 Bison bison, 15 Guernsey, 13 Jersey, 12 Bos indicus, and three Gaur individuals were included in this study for allele frequency comparisons.

Detection of single nucleotide polymorphisms (SNPs). SNPs were detected in the coding regions of the OLR1 gene by direct sequencing of RT-PCR products obtained from a pool of cDNAs from 50 animals. Total RNA was extracted from various bovine tissues, pooled, and used for RT-PCR amplification as previously described (1). The primers OLR5 (exon 1) 5'-ATGACTGTTGATGACCCCAAG-3' (SEQ ID NO: 9) and OLR6 (exon 5) 5'-CACTGTGCTCTCAATA-GATTCGCCTT-3' (SEQ ID NO: 10) were designed to amplify the total cDNA sequence (812 bp) of the gene. SNPs in the 3'UTR were detected by direct sequencing of pooled DNA samples. Pools were constructed from 220 bovine DNA samples and amplified with unlabeled primers. Primers 3 (exon 5) 5'-AAGGCGAATCTATTGAGAGC-3' (SEQ ID NO: 11) and 4 (3' UTR) 5'-ACTTCTCTGAAGTCCTGCA-3' (SEQ ID NO: 12) were used to amplify genomic DNA sequence of 270 bp in the 3'UTR. PCR and RT-PCR products were sequenced and SNPs were identified by visually inspecting sequence traces.

DNA genotyping and haplotype construction. Genomic DNA was extracted from semen samples by standard method using proteinase K and phenol/chloroform. A total of 29 sires and their 1433 sons were genotyped in this study. For polymorphism at position 1070 (A/C) of OLR1 gene (accession no. D89049) all sons were genotyped using the restriction enzyme PstI. The digestion products were run out on a 3.0% agarose gel. The A allele (uncut) was indicated by a band at 270 bp and the C allele (cut) resulted in a band at 250 bp. For polymorphism at positions 603, five sires were heterozygous (C/T), a missence mutation in which Thrionine is replaced by Methionine. For polymorphism at position 604, a synonymous substitution, eight sires were heterozygous (A/G). All sons of the five sires that were heterozygous for the missense mutation were genotyped by direct sequencing for both 603 and 604 SNPs. Intragenic haplotypes were inferred as previously described (1).

Statistical analysis. Maternal allele frequencies of OLR1 were estimated following Thaller et al. (2003), where all sons from homozygous sires and all homozygous sons of heterozygous sires were used. The allele frequencies were estimated using the formula:

$$P_c = \frac{n_{CC} + n'_{AC}}{n_{CC} + n'_{AC} + n'_{AA} + n_{AA}}$$

where $n_{CC}$ and $n_{AA}$ are the number of homozygous CC and AA sons within heterozygous sires; $n'_{AC}$ and $n'_{AA}$ are the number of heterozygous AC and homozygous AA sons from homozygous AA sires.

For single SNP analysis, weighted least squares analysis was employed to study the effects of gene variants on production and functional traits. The model was $$y_{ij} = \mu + sire_i + bx_{ij} + e_{ij}$$

where $y_{ij}$ is the PTA of the trait that was considered for son j of sire i, $sire_i$ is the fixed effect of sire i, b is the regression coefficient representing half of the gene substitution effect (Falconer and Mackey, 1996), $x_{ij}$ is the number of alleles (0, 1, or 2), and $e_{ij}$ is the residual. Reliability of the son's PTA was incorporated into the model to obtain weighted least squares estimates for the allele effects.

To test whether gene haplotypes have significant associations with the trait, an Allele Substitution Model was fitted to the PTA data (Batra et al., 1989; Weigel et al., 1990; Sharif et al., 1999). In this model, the most frequent haplotype was set to have zero effect. The allele substitution model has the structure:

$$Y_{ij} = \mu + sire_i + \sum_{k=1}^{M-1} \beta_k A_{ijk} + e_{ij}$$

where, $Y_{ij}$ is the daughter yield deviation of the trait for son j of sire i, μ is the mean; sires is the effect of sire i. $A_{ijk}=0, 1, 2$, is the number of copies of haplotype k present in the $ij^{th}$ individual, where $A_0$ represents the most frequent of M marker haplotypes, and the remaining haplotypes are denoted $A_1, \ldots A_k, \ldots, A_{(M-1)}$; $\beta_k$ are partial regression coefficients corresponding to effect of haplotype k as a deviation from the effect of the most frequent haplotype ($A_0$), which is set to zero to make the model have full rank; $e_{ij}$ is the random error associated with the $ij_{th}$ individual. This model was fitted using weighted least squares, with weights based on reliability (Israel and Weller, 1998). Significance of associations was determined for each trait separately by an F-test on the sum of squares explained by the combined effect of haplotypes. Then, for traits with significant associations, estimates of the effect of individual haplotypes, as a deviation from the effect of the most frequent haplotype, were evaluated for significance.

Real-time PCR. Expression levels of OLR1 were evaluated by real-time PCR using a GeneAmp® 5700 Sequence Detection System (PE Biosystems) and PCR products were detected with SYBR Green I (Molecular Probes). A total of 33 RNA samples obtained from heart tissues were used in the real-time quantitative RT-PCR reactions. Each PCR reaction mix (25 μl) contained 1:20,000 dilution of SYRB Green I, 2.5 μl of 10×PCR Buffer (Promega), 1.5 mM $MgCl_2$, 200 μM dNTP, 250 nM forward primer, 250 nM reverse primer, 2 μl RT-PCR products, and 1.25 U Taq polymerase (Promega) (21). Thermal cycling conditions were 95° C. for 30 sec, followed by 40 cycles at 95° C. for 30 sec, 57° C. for 30 sec, and 72° C. for 30 sec, and finally 72° C. for 10 min. Melting curve analysis and agarose gel electrophoresis were performed after real-time PCR reaction to monitor PCR product purity.

The threshold cycle ($C_T$) numbers were determined for the amplified cDNA of the bovine OLR1 mRNA and for the housekeeping gene, acidic ribosomal phosphoprotein (PO), in each sample from different tissues during real-time PCR (22). The relative quantification of OLR1 gene expression in different tissues was evaluated using a standard curve method. Standard curves for PCR amplification of cDNAs of OLR1 and PO genes were constructed using purified PCR products of the mRNAs of the two genes and five serial dilutions of the products were used ranging from 1024 to 1 attograms (23). Standard curves were generated by plotting the $C_T$ values (y-axis) against the logarithm of input purified PCR products (x-axis). For each sample, the amount of OLR1 and PO was determined from the standard curve. Then, the amount of OLR1 was divided by the amount of PO to obtain a normalized OLR1 value expressed as the ratio of OLR1/PO.

Results

Estimation of allele and haplotype frequencies in cattle breeds. Direct sequencing of pooled RT-PCR products for the total coding sequence of OLR1 revealed two SNPs in exon 4 at positions 603 (C/T) and 604 (A/G). SNP 603 is a missense mutation in which thrionine is replaced by methionine and SNP 604 is a synonymous substitution. Direct sequencing of genomic DNA at 3'UTR of OLR1 revealed one SNP (A/C) at position 1070. Four intragenic haplotypes (1=CAA; 2=CAC; 3=CGC; 4=TGC) comprising positions 603, 604, and 1070 were inferred in a sample of 633 individuals from the CDDR resource population. The frequencies of haplotype 1, 2, 3, and 4 were 0.725, 0.170, 0.052, and 0.043, respectively.

The allele frequencies of OLR1 variants at SNP 1070 were estimated in 1433 Holstein bulls, 19 Brown Swiss, 18 Bison bison, 15 Guernsey, 13 Jersey, 12 Bos indicus, and in three Gaur individuals. The C allele frequency was 0.54 (standard error=0.018) in Holstein bulls, 0.87 in Guernsey, and 0.83 in Bos indicus. The C allele was predominant in Bison bison, Brown Swiss, Jersey, and Gaur individuals. For the CDDR Holstein population, the number of sons per grandsire family ranged from 18 to 99 with an average of 49 sons per family. Seven sires were homozygous CC, eight sires were homozygous AA, and 14 sires were heterozygous.

Effects of the OLR1 haplotypes on production traits in the CDDR Holstein population. An allele substitution model, in which haplotype 1 was set to have zero effect, was used to estimate the effects of OLR1 haplotypes on milk production and health traits in Holstein population. Table 10 shows the analysis of the effects of OLR1 region which combines information of all haplotypes together. The OLR1 region as a whole showed a strong effect on fat percentage (P=0.00001), fat yield (P=0.00058), and productive life (P=0.02442). In contrast, OLR1 region did not show significant effects on milk yield, protein yield and percentage, and SCS. Table 11 shows the estimates of the substitution effects of the OLR1 haplotypes for milk production and health traits as a deviation from the effect of haplotype 1. Haplotype 2 was associated with a significant increase in fat yield (P=0.0166) and in fat percentage (P=0.0038). Haplotype 3 showed a suggestive association with productive life (0.1084) and haplotype 4 did not show significant effects on any of the examined traits.

TABLE 10

Significance of effects of OLR1 gene region on production and health traits

| Trait | F-test | P |
|---|---|---|
| Milk yield | 0.61 | 0.61187 |
| Fat yield | 5.89 | 0.00058 |
| Fat percentage | 9.28 | 0.00001 |
| Protein yield | 1.06 | 0.36462 |
| Protein percentage | 0.35 | 0.78882 |
| Productive life | 3.15 | 0.02442 |
| SCS | 1.51 | 0.21099 |

TABLE 11

Estimates of substitution effects of OLR1 haplotypes for milk production and health traits as a deviation from effect of the most frequent haplotype (1).

| Trait | Haplotype 1 | Haplotype 2 | Haplotype 3 | Haplotype 4 |
|---|---|---|---|---|
| Milk yield | 0.00 | −6.7 ± 43.9 | −3.82 ± 75.6 | −50.5 ± 65.7 |
| Fat yield | 0.00 | 3.82 ± 1.59** | −0.94 ± −0.34 | 0.46 ± 0.19 |
| Fat % | 0.00 | 0.021 ± 0.007*** | −0.004 ± 0.012 | 0.0112 ± 0.010 |
| Protein yield | 0.00 | 0.19 ± 1.09 | −0.16 ± 1.88 | −1.63 ± 1.64 |
| Protein % | 0.00 | 0.0018 ± 0.0032 | 0.0004 ± 0.0055 | −0.0004 ± 0.0048 |

TABLE 11-continued

Estimates of substitution effects of OLR1 haplotypes for milk production and health traits as a deviation from effect of the most frequent haplotype (1).

| Trait | Haplotype 1 | Haplotype 2 | Haplotype 3 | Haplotype 4 |
|---|---|---|---|---|
| Productive life | 0.00 | −0.002 ± 0.082 | 0.229 ± 0.143* | 0.126 ± 0.123 |
| SCS | 0.00 | −0.006 ± 0.012 | −0.023 ± 0.021 | −0.001 ± 0.018 |

*P = 0.1084;
**P = 0.0166;
***P = 0.0038

Effects of single SNPs on production traits. To study the effects of OLR1 variants on production and functional traits, a single SNP analysis was performed for each of the three polymorphic sites at positions 603, 604, and 1070. Analysis of SNPs 603 and 604 did not show any significant effects on any of the examined traits (data not shown). In contrast, analysis of SNP 1070 revealed significant effects on both fat yield and fat percentage.

Table 12 shows estimates of the allele substitution effects for production and functional traits in 1433 individuals from the CDDR population. Allele C was associated with a significant increase in fat yield (P=0.0013) and fat percentage (P=0.0006). It is worth noting that allele C did not show any significant unfavorable effects on the other examined traits.

TABLE 12

Estimates of allele substitution effects (of allele C at SNP 1070) and standard errors for production and functional traits in CDDR population.

| Trait | α/2 (SE) | P |
|---|---|---|
| Milk yield | −1.54 (25.08) | 0.9510 |
| Fat yield | 2.98 (0.92) | 0.0013 |
| Fat percentage | 0.014 (0.004) | 0.0006 |
| Protein yield | 0.21 (0.63) | 0.7369 |
| Protein percentage | 0.001 (0.001) | 0.5296 |
| Productive life | 0.06 (0.05) | 0.2100 |
| SCS | 0.005 (0.006) | 0.4825 |

The results on the effects of haplotype 2, which has C at position 1070, and the results of the single SNP analysis of allele C of SNP 1070 motivated us to estimate the substitution effects of haplotypes 3 and 4 for fat yield and fat percentage as a deviation from the effect of haplotype 2. These two haplotypes has also C at position 1070, hence significant differences between haplotypes 3 and 4 and haplotype 2 would point to the presence of additional SNP/s at haplotype 2 affecting fat yield and fat percentage. Table 13 shows the estimates of the substitution effects of the OLR1 haplotypes for fat yield and fat percentage as a deviation from the effect of haplotype 2. For fat yield, haplotypes 3 and 4 did not show significant associations, while for fat percentage haplotype 3 showed a suggestive association (P=0.0854) and haplotype 4 did not show significant association.

TABLE 13

Estimates of the substitution effects of the OLR1 haplotypes for fat yield and fat percentage as a deviation from the effect of haplotype 2.

| Haplotype | Fat yield | P | Fat percentage | P |
|---|---|---|---|---|
| 1 | −3.82 ± (1.59) | 0.0166 | −0.021 ± 0.007 | 0.0038 |
| 2 | 0.00 | | 0.00 | |
| 3 | −4.76 ± (3.17) | 0.1340 | −0.025 ± 0.014 | 0.0854 |
| 4 | −3.69 ± (2.74) | 0.2222 | −0.010 ± 0.012 | 0.4328 |

Expression analysis of OLRL transcripts in heart tissues. To test the expression level of OLR1 in individuals with C allele compared to individuals with T allele at SNP 1070, fetuses and dams were first genotyped using RFLP-PCR and direct genomic sequencing. Then, expression levels of OLR1 in 33 hearts from these individuals were evaluated using real-time quantitative RT-PCR (FIG. 5). The level of expression of OLR1 transcripts in relation to PO transcripts was considerably lower in individuals bearing genotype AA (OLR1/PO ratio=35.4) compared to CC individuals (OLR)/PO ratio=170.5). The OLR1/PO ratio in heterozygous individuals was 77.4. Thus, C at position 1070 in the 3'UTR may be the functional nucleotide that increases fat yield and percentage in cow milk.

In summary, nucleotide C at position 1070 in the 3' UTR of OLR1 gene has been shown to have a positive effect on milk fat yield and milk fat percentage in dairy cattle. The positional comparative candidate gene analysis and previous QTL linkage mapping results were used to select the OLR1 gene as a candidate gene affecting milk production traits. To search for polymorphic sites in the gene, pools of cDNAs extracted from a wide range of cattle tissues and pools of genomic DNA extracted from semen samples were sequenced. Using the pooled sequencing approach, two SNPs at positions 603 and 604 in exon 4 and one SNP at position 1070 in the 3' UTR were identified. SNP 603 (C/T) is a missense mutation in which thrionine is replaced by methionine and SNP 604 (A/G) is a synonymous mutation.

The first three exons of the human OLR1 correspond to cytoplasmic domain, transmembrane domain, and the neck domain whereas exons 4-6 encode the lectin-like domain (5). Chen et al. (25) conducted series of targeted mutations in the lectin-like domain to identify structures required for oxLDL binding. They found that the lectin-like domain is essential for binding and endocytosis of oxLDL. To test whether the thrionine/methionine SNP 603-found in exon 4 of the bovine gene that encodes the lectin-like domain-is associated with milk yield and composition traits, the 29 Holstein sires of the CDDR population were genotyped. Genotyping revealed five sires heterozygous for SNP 603, eight sires heterozygous for SNP 604, and 14 sires heterozygous for SNP 1070. All sons of the five sires heterozygous for SNP 603 were genotyped by direct sequencing for both 603 and 604 SNPs. Four intragenic haplotypes including SNPs 603, 604, and 1070 were identified in the CDDR population and tested for association with milk production traits. Only haplotype 2 (C-A-C) was associated with a significant increase in fat yield and fat percentage. Thus, it is concluded that the amino acid substitution at position 603 (included in haplotype 4) was not responsible for the effects of OLR1 on fat yield and fat percentage.

To search for the causative mutation in haplotype 2, two analyses were performed; a single SNP analysis for each of the three individual SNPs and a haplotype analysis. The results of the single SNP analysis showed that allele C of SNP 1070 had significant effects on fat yield and percentage whereas SNPs 603 and 604 had no significant effects. Given that haplotypes 2, 3 and 4 include C nucleotide at position 1070 and that only haplotype 2 showed significant associations, the allele substitution model was used to estimate the effects of haplotypes 3 and 4 as a deviation from the effect of haplotype 2. The results show that the effects of haplotype 2 were not significantly different from the effects of haplotypes 3 and 4. Thus, both single SNP analysis and haplotype analysis strongly indicate that SNP 1070 in the 3'UTR might be the causative mutation affecting milk fat yield and percentage. To search for other SNPs in the 3'UTR, a total of 790 bp of genomic DNA from all 29 sires were sequenced, but no SNPs were identified.

To provide support for the hypothesis that SNP 1070 is the QTN responsible for OLR1 effects, the expression levels of OLR1 in individuals bearing different genotypes were assessed. It was found that OLR1 expression was reduced in AA individuals compared to CC and AC individuals, suggesting that A at position 1070 may be the nucleotide decreasing OLR1 expression.

It is of note that two independent studies on the human gene reported, surprisingly, that a SNP(C/T) in the 3' UTR, at position 1073, was associated with Alzheimer's disease (AD). Luedecking-Zimmer et al. (25) reported that among three SNPs identified in OLRJ, the 3'UTR polymorphism showed the most significant association with AD. Moreover, they showed that the C allele at this position had a higher affinity for binding regulatory proteins compared to the T allele. Also, Lambert et al. (26) presented additional evidence that the 3' UTR polymorphism was associated with AD. Using electrophoretic mobility shift assays, they found that the C allele was associated with higher binding affinity of nuclear proteins. In addition, they showed that the expression level of OLR1 was lower in individuals bearing CC genotypes compared to CT and TT individuals.

The exact mechanism by which the bovine OLR1 variants can affect milk fat yield and milk fat percentage is not clear. However, given that OLR1 is a receptor for oxLDL and that it is expressed abundantly in heart, it might affect directly the metabolism of oxLDL which in turn affects fat metabolism. In fact, the hypothesis that human OLR1 variants might be involved in heart diseases was tested in two independent studies. Mango et al. (27) showed that the 3' UTR SNP was associated with higher risk of developing acute myocardial infarction. Also, Chen et al. (28) reported association of the 3'UTR SNP with coronary artery disease. Moreover, using electrophoretic mobility shift assay, they found that the 3' UTR SNP affects the binding of a putative transcription factor in an allele-specific manner. Thus, while not willing to be bound by any theory, it is believed that the 3' UTR SNP of the present invention that affects milk fat yield and milk fat percentage, might affect mRNA stability or translation of the OLR1 as it was predicted for the human gene (28). There is growing evidence that 3' UTR sequences are involved in the regulation of gene expression and they can control stability of mRNA, polyadenylation, rates of translation, nuclear transport, and gene silencing (29). Recently, Oliver et al. (30) reported that a 3'UTR polymorphism in the Gpc3 gene, a candidate gene chosen based on QTL studies, affects high growth in mice.

Estimation of allele frequencies of OLR1 in different cattle breeds was an additional support for the hypothesis that SNP 1070 is the actual QTN affecting fat yield and percentage. It has long been known that Bison bison, Brown Swiss, Jersey, and Guernsey breeds have higher fat percentage than the Holstein breed. Surprisingly, it was found that the frequency of the C allele of SNP 1070—that is associated with an increase in fat yield and fat percentage in the Holstein population—was 54% in the Holsteins, whereas its frequency in Bison bison, Brown Swiss, and Jersey populations was 100% and its frequency in Guernsey was 87%.

Thus, several lines of evidence show that SNP 1070 is the QTN.

References to Example 4
1. Mehta, J. L. & Li, D. Y. (1998) Identification and autoregulation of receptor for OX-LDL in cultured human coronary artery endothelial cells. *Biochem. Biophys. Res. Commun.* 248, 511-514.
2. Imanishi, T., Hano, T., Sawamura, T., Takarada, S. & Nishio I. (2002) Oxidized low density lipoprotein potentiation of Fas-induced apoptosis through lectin-like oxidized-low density lipoprotein receptor-1 in human umbilical vascular endothelial cells. *Circ. J.* 66, 1060-1064.
3. Sawamura, T., Kume, N., Aoyama, T., Moriwaki, H., Hoshikawa, H., Aiba, Y., Tanaka, T., Miwa, S., Katsura, Y., Kita, T. et al. (1997) An endothelial receptor for oxidized low-density lipoprotein. *Nature* 386, 73-77.
4. Oka, K., Sawamura, T., Kikuta, K., Itokawa, S., Kume, N., Kita, T. & Masaki, T. (1998) Lectin-like oxidized low-density lipoprotein receptor 1 mediates phagocytosis of aged/apoptotic cells in endothelial cells. *Proc. Natl. Acad. Sci. USA* 95, 9535-9540.
5. Aoyama, T., Sawamura, T., Furutani, Y., Matsuoka, R., Yoshida, M. C., Fujiwara, H. & Masaki, T. (1999) Structure and chromosomal assignment of the human lectin-like oxidized low-density-lipoprotein receptor-1 (LOX-1) gene. *Biochem. J.* 339, 177-84.
6. Khatkar, M. S., Thomson, P. C., Tammen, I. & Raadsma, H. W. (2004) Quantitative trait loci mapping in dairy cattle: review and meta-analysis. *Genet. Sel. Evol.* 36, 163-190.
7. Heyen, D. W., Weller, J. I., Ron, M., Band, M., Beever, J. E., Feldmesser, E., Da, Y., Wiggans, G. R., VanRaden, P. M. & Lewin, H. A. (1999) A genome scan for QTL influencing milk production and health traits in dairy cattle. *Physiol. Genomics* 1, 165-175.
8. Olsen, H. G., Gomez-Raya, L., Vage, D. I., Olsaker, I., Klungland, H., Svendsen, M., Adnoy, T., Sabry, A., Klemetsdal, G. Schulman, N. et al. (2002) A genome scan for quantitative trait loci affecting milk production in Norwegian dairy cattle. *J. Dairy Sci.* 85, 3124-3130.
9. Ashwell, M. S., Heyen, D. W., Sonstegard, T. S., Van Tassell, C. P., Da, Y., VanRaden, P. M., Ron, M., Weller, J. I. & Lewin, H. A. (2004) Detection of quantitative trait loci affecting milk production, health, and reproductive traits in Holstein cattle. *J. Dairy Sci.* 87, 468-475.
10. de Koning, D. J., Schulmant, N. F., Elo, K., Moisio, S., Kinos. R., Vilkki, J., & Maki-Tanila, A. (2001) Mapping of multiple quantitative trait loci by simple regression in half-sib designs. *J. Anim Sci.* 79, 616-622.
11. Viitala, S. M., Schulman, N. F., de Koning, D. J., Elo, K., Kinos, R., Virta, A., Virta, J., Maki-Tanila, A. & Vilkki J.

H. (2003) Quantitative trait loci affecting milk production traits in Finnish Ayrshire dairy cattle. *J. Dairy Sci.* 86, 1828-1836.

12. Bennewitz, J., Reinsch, N., Grohs, C., Leveziel. H., Malafosse, A., Thomsen, H., Xu, N., Looft, C., Kuhn, C., Brockmann, G. A. et al. (2003) Combined analysis of data from two granddaughter designs: A simple strategy for QTL confirmation and increasing experimental power in dairy cattle. *Genet. Sel. Evol.* 35, 319-338.

13. Rodriguez-Zas, S. L., Southey, B. R., Heyen, D. W. & Lewin, H. A. (2002) Interval and composite interval mapping of somatic cell score, yield, and components of milk in dairy cattle. *J. Dairy Sci.* 85, 3081-3891.

14. Khatib, H., Heifetz, E. & Dekkers, J. C. (2005) Association of the protease inhibitor gene with production traits in Holstein dairy cattle. *J. Dairy Sci.* 88, 1208-1213.

15. Thaller, G., Kramer, W., Winter, A., Kaupe, B., Erhardt, G. & Fries, R. (2003) Effects of DGAT1 variants on milk production traits in German cattle breeds. *J. Anim Sci.* 81, 1911-1918.

16. Falconer, D. S. & Mackay T. F. C. (1996) *Quantitative genetics*. (Addison Wesley Longman Ltd., Essex, England).

17. Batra, T. R., Lee, A. J. & Gavora, J. S. (1989). Class I alleles of the bovine major histocompatibility system and their association with economic traits. *J. Dairy Sci.* 72, 2115-2124.

18. Weigel, K. A., Kehrli, M. E. J. R., Stear, M. J. & Kelley, D. H. (1990) Association of class I bovine lymphocyte antigen complex alleles with health and production traits in dairy cattle. *J. Dairy Sci.* 73, 2538-2546.

19. Sharif S., Mallard B. A., Wilkie, B. N., Sargeant, J. M., Scott, H. H., Dekkers, J. C. & Leslie, K. E. (1999) Association of the bovine major histocompatibility complex DRB3 (BoLA-DRB3) with production traits in Canadian dairy cattle. *Animal Genetics* 30, 157-160.

20. Israel, C. & Weller, J. I. (1998) Estimation of candidate gene effects in dairy cattle populations. *J. Dairy Sci.* 81, 1653-1662.

21. Karsai, A., Muller, S., Platz, S. & Hauser, M. T. (2002) Evaluation of a homemade SYBR green I reaction mixture for real-time PCR quantification of gene expression. *Biotechniques* 32, 790-796.

22. Bieche, I., Nogues, C., Paradis, V., Olivi, M., Bedossa, P., Lidereau, R. & Vidaud, M. (2000) Quantitation of hTERT gene expression in sporadic breast tumors with a real-time reverse transcription-polymerase chain reaction assay. *Clin. Cancer Res.* 6, 452-459.

23. Robert, C., McGraw, S., Massicotte, L., Pravetoni, M., Gandolfi, F. & Sirard, M. A. (2002) Quantification of Housekeeping Transcript Levels During the Development of Bovine Preimplantation Embryos. *Biol. Reprod.* 67, 1465-1472.

24. Chen, M., Narumiya, S., Masaki, T. & Sawamura, T. (2001) Conserved C-terminal residues within the lectin-like domain of LOX-1 are essential for oxidized low-density-lipoprotein binding. *Biochem J.* 355, 289-296.

25. Luedecking-Zimmer, E., DeKosky, S. T., Chen, Q., Barmada, M. M. & Kamboh, M. I. (2002) Investigation of oxidized LDL-receptor 1 (OLR1) as the candidate gene for Alzheimer's disease on chromosome 12. *Hum. Genet.* 111, 443-451.

26. Lambert, J. C., Luedecking-Zimmer, E., Merrot, S., Hayes, A., Thaker, U., Desai, P., Houzet, A., Hermant, X., Cottel, D., Pritchard, A. et al. (2003) Association of 3'-UTR polymorphisms of the oxidised LDL receptor 1 (OLR1) gene with Alzheimer's disease. *J. Med. Genet.* 40, 424-430.

27. Mango, R., Clementi, F., Borgiani, P., Forleo, G. B., Federici, M., Contino, G., Giardina, E., Garza, L., Fahdi, I. E., Lauro, R. Et al. (2003) Association of single nucleotide polymorphisms in the oxidised LDL receptor 1 (OLR1) gene in patients with acute myocardial infarction. *J. Med. Genet.* 40, 933-936.

28. Chen, Q., Reis, S. E., Kammerer, C., Craig, W. Y., LaPierre, S. E., Zimmer, E. L., McNamara, D. M., Pauly, D. F., Sharaf, B., Holubkov, R. et al. (2003) Genetic variation in lectin-like oxidized low-density lipoprotein receptor 1 (LOX1) gene and the risk of coronary artery disease. *Circulation* 107, 3146-3151.

29. Conne, B., Stutz, A. & Vassalli, J. D. (2000) The 3' untranslated region of messenger RNA: A molecular 'hotspot' for pathology? *Nat. Med.* 6, 637-641.

30. Oliver, F., Christians, J. K., Liu, X., Rhind, S., Verma, V., Davison, C., Brown, S. D., Denny, P. & Keightley, P. D. (2005) Regulatory variation at glypican-3 underlies a major growth QTL in mice. *PLoS. Biol.* 3, e135.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations and equivalents falling within the scope of the appended claims and equivalents thereof. All references cited hereinabove and/or listed below are hereby expressly incorporated by reference.

What is claimed is:

1. A method for selectively breeding of cattle using a multiple ovulation and embryo transfer procedure (MOET), the method comprising superovulating a female animal, collecting eggs from superovulated female, in vitro fertilizing said eggs using semen from a suitable male animal, implanting fertilized eggs into other females allowing for an embryo to develop, and detecting single nucleotide polymorphism (SNP) in uterine milk protein (UTMP) coding sequence of the developing embryo by determining the identity of a nucleotide at position 1296 of the UTMP coding sequence (SEQ ID NO: 1) and comparing the identity to the nucleotide identity at a corresponding position of SEQ ID NO: 1, and terminating pregnancy if said developing embryo does not have guanine at position 1296 of the UTMP coding sequence.

2. The method according to claim 1, further comprising determining whether the developing embryo is homozygous with regard to the SNP, and terminating pregnancy if the embryo is not homozygous with regard to the SNP.

3. A method for selectively breeding dairy cattle, comprising selecting a bull that homozygously has guanine at position 1296 of bovine uterine milk protein (UTMP) coding sequence (SEQ ID NO: 1), and using its semen for fertilizing a female animal.

4. The method according to claim 3, wherein a bull is selected that further homozygously has cytosine at position 603, adenosine at position 604 and cytosine at position 1070 of a bovine lectin-like oxidized LDL receptor (OLR1) coding sequence (SEQ ID NO: 4).

5. The method according to claim 3, wherein the female animal also has homozygously guanine at position 1296.

6. The method according to claim 3, wherein the female animal is in vitro fertilized.

7. A method for testing a dairy cattle for increased productive life, comprising detecting single nucleotide polymorphism (SNP) in uterine milk protein (UTMP) coding sequence of a cell of the dairy cattle by determining the identity of a nucleotide at position 1296 of the UTMP coding sequence (SEQ ID NO: 1), wherein a cattle has guanine at position 1296 of bovine uterine milk protein (UTMP) coding sequence (SEQ ID NO: 1) indicates that the cattle has increased productive life.

8. The method of claim 1, for breeding cattle for increased productive life.

* * * * *

SEQUENCE LISTING

```
<160> NUMBER OF SEQ ID NOS: 12

<210> SEQ ID NO 1
<211> LENGTH: 1463
<212> TYPE: DNA
<213> ORGANISM: Bos taurus

<400> SEQUENCE: 1
ggctggattg ccgcagaaat gtcccacggg agaatgaatc tggccctgtc tctggtcttc      60
atcctctgtg gcctgtttaa tagcatcttc tgtgaaaagc aacaacactc tcaaaagcac     120
atgaacctag tcttattaaa gaaaatttca gctctctccc agaagatgga agctcaccct     180
```

```
aaggattttg cccaagaatt gttcaaggct ttgataattg aggatcccag aaagaatatc      240
atcttctccc ccatggccat gaccaccacc ctggccaccc tctccctggg gatcaagtct      300
acaatgagaa cccaccaccc tgaggacctg aaacttgagc ccaaactgtt ggatgtgcac      360
aagtacttac agcctctggt ccacgtgggg cgtgagctag tgaagcagaa ggtactgaag      420
caccagcaca ttctctttat caacagaaaa atgatggtca accagatgct tctacagcag      480
ataagcaagc tgcagggaat ggacatccag atgattgact ttacagatat agaaaaagcc      540
aagaagacca tcagccacca tgtggctgaa aaaacacata cgaaaatcac aaacttaatc      600
accgacctga accctgagac catcctgtgt cttgttaacc acattttctt caaaggcatc      660
ttgaaaagag cttttcagcc caaactcacc cagaaggagg tcttctttgt gaatgaccaa      720
accaaagtgc aggtggacat gatgagaaag acagaacgga tgctttacag ccggtcagag      780
gagctacatg ctacgatggt taagatgcct tgcaaaggaa atgtgtccct aactctcatg      840
cttccagatg ccggacaatt tgacactgat cttaaaaaga tgactgctaa gcgagctaaa      900
cttcagaaaa tcagtgactt cagactggtg cgcttaattt tgcccaagtt gaagatctcc      960
ttcaagataa actttaagca tctgcttccc aagattgacc ccaaacatat actgactgcc     1020
acagcaatct cacaggccat cacatcgaag gctcccctgc ctaatttgga ggccctacat     1080
caagctgaga tagagctgag cgagcacgcc ttaaccgtgg acacagccat tcacacagat     1140
aatctgttga aagtcccagt gaaggcaaag gaggtcccgg cggtcgtgaa agtcccaatg     1200
aaggcaaagg aggtcccggc ggtcgtgaaa gtcccaatga acacaaagga ggtcccagtg     1260
gtcgtgaaag tcccaatgaa cacaaaggag gtcccagtgg tcgtgaaggt caacagaccc     1320
ttcttgctgt tgtggagga tgagaagact caaagagacc tctttgtggg caaagtcctc     1380 aaccccaag ttgagtagag ccagggccac actgtgcagc acaggaactt agcaggccat     1440
gaataaaaag agtacaattc acc                                             1463

<210> SEQ ID NO 2
<211> LENGTH: 626
<212> TYPE: DNA
<213> ORGANISM: Bos taurus

<400> SEQUENCE: 2
ctttaaatat agcctcaagt ttgccagtgg cttgcctgtg aaatagtgca aagctgtcct       60
gtatctgggc agaggataaa agttatgtgt gttattatat tttccacact ggccattgaa      120
aactaaagat tctctttctt gggagaatta gcttttggta tggctttatg atgctggcta      180
atatcaatag aaggaagtaa actttacaaa ttcatgagta gtatcttcca tttcagcttt      240
aataccaaag ttgaatatat tctgccttca tcatgaaatt gaagttagta aatgaaactg      300
tcttcacagt tctatcaagg gagccaaact attaacagct ctcttaaggc aaatcctatt      360
attttttcaa aaagttgaaa ttaattgtag atgtaaacaa actcagaaat ttaatgcatg      420
tttcataagt gggttcactt gtctttattg tttagtaaaa attttaaaat tgagaagaaa      480
aactagtaat tgacaaatca ttaggtggag attatgagaa tccataatt tgaaaactca       540 tcctgtgtaa ctgccttgag aattgggtaa ttttcactgg caaatgtgta tctctcacaa      600
atacattaca gatggttcca ctaaaa                                           626

<210> SEQ ID NO 3
<211> LENGTH: 1560
<212> TYPE: DNA
<213> ORGANISM: Bos taurus
```

<400> SEQUENCE: 3

```
taattaactc taaatattaa aattctcaca attaaagaac aaccactcca aaaaatagcc    60
accaagcagg ccatttgggc tggttaaatg gatcttccct gcctgttggg cttccctgat   120
agctcagttg gtaaagcatc tgcctgcaac ttggaagacc cgggttcagt ccctgggtcg   180
ggaagactcc ctggagaagg aaatggcaac cccctctagt actcttgcct ggaaaatttc   240
catggactga ggaccctggt aggctaagag tcagacagaa ctgagcaact tcacttcact   300
ttcctgcctg tttgtaaaag tgagcttagg acaccaattg atctgtcagg ttgtcttccg   360
gcttaatcct tccacaatga ggctagaaaa ataagacctg ctttggatgg aaacagctaa   420
cttttgaata aaaagttac gttgtatgat gtgcactgat ttgtgtcttt tcttcttcag    480
aattctgtgt cctctgagga aactgatgac aacaaacaaa atgtgagtct ttgctttgat   540
tctgatgtct gttgtgcctt agactcagga aggcactctt tctcctaatg acattgccca   600
ggttcaaatt ccggcaaaat tccactagca aacccttcag gaactacttt ttattgggac   660
tattaatagg gataagttaa atttgctttc cttaagattc tatttgaaga tgctgagaat   720
ctataagaga agttagataa atgacccagg atatttgcaa atcagaagtg tgatagacat   780
taactgagct atagtttcta cacatggata agagagtcac cttttgatta ccaggctaa    840
tagggaggtg atttttagttt tgggggtgtg cattaataca tggattctct gatccctga    900
gaattttcat ttcaaataga aaaggtagtc tcacaattat gtatctgtat ttattggatc    960
attgaaattt ggtaaattag tgtttattat gaacaaggaa aaacagtgtc attgatacaa   1020
atattataac tcatacgttt ggcttgaaaa tatctgtgaa atcgttttt atgagaaacc    1080
aagaaaaatg ccttagaata ggattccatt taccccttgtg ttaaagggga aattggaata   1140
agctcatttt agcatttaaa agccattaag tgctttgttg tgaatacaaa gattctaaaa   1200
ctaaataaag atagtaaaat actaatgcac tgtaaagcct aagggacagt aaaaaccctg   1260
acacccattt ttctggccat cttgatttct agaccctccc aagtaagtcc aatgaaagcc    1320
ctgagcaaac agacgatcta gatgacgatg atgataacag ccaggacgtc aactctaatg   1380
actccgacga cgctgaaacc actgatgacc ctgaccattc cgacgagtct caccattctg   1440
atgaatctga tgaagttgat ttcccactg atattccaac aatcgcagtt ttcactccgt   1500
ttatccctac ggaaagcgca atgatggcc gaggtgatag tgtggcttac ggactgaagt   1560
```

<210> SEQ ID NO 4
<211> LENGTH: 1879
<212> TYPE: DNA
<213> ORGANISM: Bos taurus

<400> SEQUENCE: 4

```
gcttcactct ctcattcttg gaatacattt gaaaatgact gttgatgacc ccaagggtat    60
gaaagatcaa cttgatcaga agccaaatgg caagacagca aaaggttttg tttcctcttg    120
gaggtggtac cctgctgctg tgactctagg ggtcctttgt ctgggattac tggtgactgt    180
tatattgttg atactgcaat tatcccaggt ctctgatctc ataaagaaac agcaagcaaa   240
tattactcac caggaagata tcctggaggg acagatttta gcccagcgcc gatcagaaaa   300
atctgcccag gagtcacaga aggaactcaa agaaatgata gaaacccttg cccacaagct   360
ggatgagaaa tccaagaaac taatggaact tcaccgccag aacctgaatc tccaagaagt   420
tctgaaagag gcagcaaact attcaggtcc ttgtccccaa gactggctct ggcatgaaga   480
```

-continued

| | |
|---|---|
| aaactgttac caattttcct ctggctcttt taattgggaa aaaagccagg agaactgctt | 540 |
| gtctttggat gcccacttgc tgaagattaa tagcacagat gaactggaat tcatccagca | 600 |
| aatgattgcc cattccagtt tccccttctg gatggggttg tcaatgagga aacccaatta | 660 |
| ctcgtggctt tgggaagatg gtactccttt gacgccccac ttgtttagaa ttcagggagc | 720 |
| tgtttcccgt atgtatcctt cagggacctg tgcatatatt caaaggggaa ctgttttttgc | 780 |
| tgaaaactgc attttaactg cattcagtat atgtcaaaag aaggcgaatc tattgagagc | 840 |
| acagtgaatt tgaaggatct ggaggaaaag aaggaaacct tgaattctc ttctggaatt | 900 |
| taagctatac ttcatcactt agatgtaaac cattagagcc cagggaaatg cctgctactg | 960 |
| gttgagtgca gaactcctta gcagagactg gcccagctgc ctggcacctt gatagcaaaa | 1020 |
| gttgcaattc cctctgtata ttttttcccta acttgttcca gtcctcccc tgcaggactt | 1080 |
| cagagaagtc aattttttctg tttccattgt ttctaagaac ttgttgccta actcaaggtc | 1140 |
| acagcatttt tctcactttt gtcctatgct ttccttctagg cattgtagag ttttagattt | 1200 |
| tacatggaaa tctagaactt attttagatt aatttctaag tgatatatgg atgtatggaa | 1260 |
| gttttctgtt tgttttttgc ttgtgagtat tcaattgttt ttgcaacatt tgctgaaaag | 1320 |
| actattcttc cttcactaca ttgcctttgc actgttgtca acaattatcc atacatgcct | 1380 |
| ggctctattt ctggattttc tattcctttc catttattta tttattattc ttggcttaca | 1440 |
| acatcaccat gatattttga attctatggt tctttaatat atcttggaat cacatggtag | 1500 |
| tagttattca ttgttgttct tttttagagt tgtttggtta atctatgctt ttgtatttct | 1560 |
| gtcttaaatt ggcttgtcca tttctaaaaa aacttgaaat tttgaattgc actgaatcca | 1620 |
| tacataaatt tagggaaaat tgaattctta aaaatactga tttgttcaac tcatgaaaaa | 1680 |
| ggtgtattgc tctatttagg tattccttat tttctttaag caatgctttt taatgttctt | 1740 |
| tgtgtagata ttgttagatt atcatcatgt atttcacatt atttatgcta ctgtagatag | 1800 |
| tattgttatc atttgttgtt cttattttca aagtcttctg ctagtatgta gaattataat | 1860 |
| aaagtttgat attaatatt | 1879 |

```
<210> SEQ ID NO 5
<211> LENGTH: 20
<212> TYPE: DNA
<213> ORGANISM: Artificial
<220> FEATURE:
<223> OTHER INFORMATION: Oligonucleotide primer

<400> SEQUENCE: 5
```

| | |
|---|---|
| gcctcaagtt tgccagtggc | 20 |

```
<210> SEQ ID NO 6
<211> LENGTH: 20
<212> TYPE: DNA
<213> ORGANISM: Artificial
<220> FEATURE:
<223> OTHER INFORMATION: Oligonucleotide primer

<400> SEQUENCE: 6
```

| | |
|---|---|
| ggctcccttg atagaactgt | 20 |

```
<210> SEQ ID NO 7
<211> LENGTH: 22
<212> TYPE: DNA
<213> ORGANISM: Artificial
<220> FEATURE:
<223> OTHER INFORMATION: oligonucleotide primer
```

```
<400> SEQUENCE: 7
gcaaatcaga agtgtgatag ac                                              22

<210> SEQ ID NO 8
<211> LENGTH: 20
<212> TYPE: DNA
<213> ORGANISM: Artificial
<220> FEATURE:
<223> OTHER INFORMATION: Oligonucleotide primer

<400> SEQUENCE: 8
ccaagccaaa cgtatgagtt                                                 20

<210> SEQ ID NO 9
<211> LENGTH: 21
<212> TYPE: DNA
<213> ORGANISM: Artificial
<220> FEATURE:
<223> OTHER INFORMATION: Oligonucleotide primer

<400> SEQUENCE: 9
atgactgttg atgaccccaa g                                               21

<210> SEQ ID NO 10
<211> LENGTH: 26
<212> TYPE: DNA
<213> ORGANISM: Artificial
<220> FEATURE:
<223> OTHER INFORMATION: Oligonucleotide primer

<400> SEQUENCE: 10
cactgtgctc tcaatagatt cgcctt                                          26

<210> SEQ ID NO 11
<211> LENGTH: 20
<212> TYPE: DNA
<213> ORGANISM: Artificial
<220> FEATURE:
<223> OTHER INFORMATION: Oligonucleotide primer

<400> SEQUENCE: 11
aaggcgaatc tattgagagc                                                 20

<210> SEQ ID NO 12
<211> LENGTH: 19
<212> TYPE: DNA
<213> ORGANISM: Artificial
<220> FEATURE:
<223> OTHER INFORMATION: Oligonucleotide primer

<400> SEQUENCE: 12
acttctctga agtcctgca                                                  19
```